United States Patent [19]
Giese

[11] Patent Number: 5,360,819
[45] Date of Patent: Nov. 1, 1994

[54] MOLECULAR ANALYTICAL RELEASE TAGS AND THEIR USE IN CHEMICAL ANALYSIS

[75] Inventor: Roger W. Giese, Quincy, Mass.

[73] Assignee: Northeastern University, Boston, Mass.

[21] Appl. No.: 710,318

[22] Filed: Mar. 11, 1985

Related U.S. Application Data

[63] Continuation-in-part of Ser. No. 344,394, Feb. 1, 1982, Pat. No. 4,709,016.

[51] Int. Cl.⁵ .............................................. A01N 37/12
[52] U.S. Cl. .................................... 514/538; 546/226; 562/465; 562/840; 568/355; 568/647; 560/60; 514/423
[58] Field of Search ............... 514/538, 423; 546/226; 562/465, 840; 560/60; 568/355, 647

[56] References Cited

U.S. PATENT DOCUMENTS

| | | | |
|---|---|---|---|
| 4,171,311 | 10/1979 | Araps | 260/326.34 |
| 4,182,656 | 1/1980 | Ahnell | 435/34 |
| 4,230,797 | 10/1980 | Boguslaski | 435/7 |
| 4,231,999 | 11/1980 | Carlsson | 424/1 |
| 4,261,893 | 4/1981 | Boguslaski | 260/326 |
| 4,279,992 | 7/1981 | Boguslaski | 435/7 |
| 4,296,120 | 10/1981 | Kadin | 514/423 |
| 4,296,129 | 10/1981 | Kadin | 514/538 |
| 4,318,981 | 3/1982 | Burd | 435/7 |
| 4,331,590 | 5/1982 | Bocuslaski | 260/112 B |
| 4,360,592 | 11/1982 | Weltman | 435/7 |
| 4,423,143 | 12/1983 | Rubenstein | 435/7 |
| 4,650,750 | 3/1987 | Giese | 435/7 |
| 4,709,016 | 11/1987 | Giese | 530/389 |

FOREIGN PATENT DOCUMENTS

| | | |
|---|---|---|
| 2618511 | 11/1976 | Germany . |
| 2901173 | 1/1979 | Germany . |
| 2839836 | 3/1979 | Germany . |
| 2839883 | 3/1979 | Germany . |
| 2839884 | 3/1979 | Germany . |

OTHER PUBLICATIONS

CA 94(9); 65275d 1979.
Barrett, A. G. M. et al. J. C. S. Perkin I (3) pp. 662–668, 1979.
Carlsson, Biochem. J., 173, pp. 723–737, (1978), "Protein Thiolation and Reversible Protein–Protein Conjugation".
Poole, Anal. Chem., 52(9), pp. 1002–1016, (1980), "Derivatization Techniques for the Electron–Capture Detector".
Giese, abstract for C&EN 183rd ACS national meeting Mar. 28–Apr. 2 presentation–Release Tags: a New Class of Analytical Reagents (Feb. 15, 1982).
Giese et al, Clinical Chemistry, 28(9), pp. 1844–1847, (1982), "Release Tags: a New Class of Analytical Reagents".
Giese, Trends in Analytical Chemistry, 2(7), pp. 166–168 (1983), "Electrophoric release tags: ultrasensitive molecular labels providing multiplicity".
Thiesen, Analytical Biochemistry, 152, pp. 211–214, (1986), "Sequential Detection of Antigens in Western Blots with Differently Colored Products".
Cohen, Analytical Chemistry, 54(8), p. 890, (1982), Editors' Column, "New Clinical Applications for Familiar Analytical Concepts".

(List continued on next page.)

Primary Examiner—Paul J. Killos
Attorney, Agent, or Firm—Weingarten, Schurgin, Gagnebin & Hayes

[57] ABSTRACT

A release tag reagent suitable for use in the chemical analysis of a substance to be detected, which substance contains reactive groups, such as for, but not limited to gas phase detection groups, which reagent comprises three covalently bonded groups: a signal group which on release provides a ketone signal compound to be detected, a release group which may be cleaved to release the ketone signal group, which release group contains, for example, a vic glycol or an olefin group and a reactivity group which is reactive with a reactive group of the substance to be detected.

20 Claims, No Drawings

OTHER PUBLICATIONS

BioRad Catalog, 1986, "Blotting Media".
Meeting Briefs from New York, C&EN, Apr. 28, 1986, "Reagents function as electrophoric labels".
Meriwether, Clinical Chemistry News, 8(6), (Jun. 1982), "Release Tags" column on Advanced Concepts at Oak Ridge Conference.
Parks, Cytometry, 5(159), pp. 159-168, (1984), "Three-Color Immunofluorescence Analysis of Mouse B-Lymphocyte Subpopulations".
Boorsma, J. of Microscopy, 143(2), pp. 197—203, (1986), "Simultaneous immunoenzyme double labelling using two different enzymes linked directly to monoclonal antibodies or with biotin-avidin".
Newallis, J. Org. Chem., 30, pp. 3834-3837, (1965), "Fluoro Ketones. III. Preparation and Thermal Decomposition of Fluoroacetone Hemiketal Esters".
Yates, J. Org. Chem., 34, p. 2566?, (1969), "The Thermal Decomposition of $\beta$-Hydroxy Ketones".
Yates, J. Org. Chem. 36, pp. 3379-3382, (1971), "The Thermal Decomposition of $\beta$-Hydroxy Esters".
Arnold, J. Am. Chem. Soc., 81, pp. 6443-6445, (1959). "The Pyrolysis of $\beta$-Hydroxyolefins".
Smith, Nature, 321, pp. 674-679, (1986), "Fluorescence detection in automated DNA sequence analysis".
Goralski, NEN Product News, 3(4), pp. 2-3, (Jun. 1984), "Repetitive Screening of the Drosophila Genomic Library".
Haase, Science, 227, pp. 189-192, (Jan. 1985), "Detection of Two Viral Genomes in Single Cells by Double-Label Hybridization in Situ and Color Microradioautography" (abstract).
Peterson, Science, 227, pp. 1361-1364, (Mar. 1985), "Multiple Stable Isotopes Used to Trace the Flow of Organic Matter in Estuarine Food Webs" (abstract).
Sidki, Therapeutic Drug Monitoring, 7, pp. 101-107, (1985), "Dual-Label Fluoroimmunoassay for Simultaneous Determination of Primidone and Phenobarbital".
Biochem., 13, p. 5159, (1974)*.
Biochem. J., 165, p. 479, (1977)*.
Science, 198, p. 1056, (1977)*.
Proc. Soc. Exp. Biol. Med., 155, p. 287, (1977)*.
Gross, "The Peptide" (1981), later translation of Helv. Chim. Acta, 41, p. 491, (1958)*.
Proc. National Acad, Sci., 72, (1975)*.
Tetrahedron Letters, 46, (1973)*.
FACSS, Final Program Special Events Abstracts, 9th annual meeting Sep. 19-24, 1982, Philadelphia, Pa.*.
"Edman Degradation" from L. Stryer, Biochemistry, W. H. Freeman & Co.: San Francisco, 1981, p. 24.
Anthony G. M. Barrett, et al., "Phenol Oxidation and Biosynthesis. Part 27. Reactions of Relevance to the Formation of Erysodienone in vitro" in Journal of The Chemical Society, Perkin Transactions I, 3, pp. 662-668, 1979.

MOLECULAR ANALYTICAL RELEASE TAGS AND THEIR USE IN CHEMICAL ANALYSIS

ACKNOWLEDGEMENT

The U.S. Government has rights in this invention pursuant to Grant No. AM 21797, awarded by the U.S. Department of Health, Education and Welfare and under DARPA contracts N00014-82-K-0811 and N00014-84-C-0254 administered by the Office of Naval Research.

REFERENCE TO PRIOR APPLICATIONS

This application is a continuation-in-part of U.S. patent application Ser. No. 344,394, filed Feb. 1, 1982, hereby incorporated by reference. The parent application relates to release tag compounds, particularly release tag compounds with a polyhalo such as a polyfluoro signal release group, such as a polyfluorobenzoyl group, a release group, subject to cleavage by a chemical reaction such as an olefin, vic glycol, a methionyl release group and a reactivity group, such as a reactivity group reactive with an OH or amino group or other reactive group of a substance, such as a N-hydroxysuccinimide group to form a covalent bond therewith.

FIELD OF THE INVENTION

This invention relates to chemical analysis, both qualitative and quantitative, and, more particularly, to a new class of release tag reagents serving as molecular labels or tags in analytical procedures and to ketone signal compounds to be detected by chemical analysis.

BACKGROUND OF THE INVENTION

Sensitive and specific chemical labels or signal groups are widely used in chemical analysis. These labels include radioactive atoms, fluorescent reagents, luminescent molecules, metal-containing compounds, electron absorbing substances, and light absorbing compounds. In each case, one or more techniques are available to measure the particular label of interest. For example, in the case of electron-absorbing labels, measurements can be carried out by gas chromatography with electron capture detection (GC-ECD).

Not all analytical procedures involve the use of such chemical labels, but generally those applicable procedures can be divided into three broad categories. In the first category, the substance to be measured (analyte substance or analyte) is reacted with the label during the analytical procedure, leading to a labeled analyte. The signal from this labeled analyte then provides a measurement of the analyte substance. In the second category, the analyte in the sample is not labeled, but a labeled internal standard, labeled comparison substance, or labeled specific binding partner is employed in the procedure. An example of the second category is the use of chemical tracers in radioimmunoassay procedures. The third analytical category is exemplified by the double isotope derivative technique. This technique involves both labeling of the analyte and the use of one or more labeled internal standards. The labeled internal standard substances may be labeled additionally in this isotope derivative procedure along with the analyte.

There are major shortcomings associated with each of the types of chemical labels currently employed in analytical procedures. For example, the use of radiolabels, particularly the more sensitive radiolabels like $^{125}I$, is limited by their short half-lives; by the physical instability and tendency for chemical lability with these labels; by safety and disposal considerations; and by the unavailability of several, closely related forms which can be measured simultaneously with comparable sensitivity and complete discrimination. Radiolabels like $^3H$ or $^{14}C$ are limited in these same respects (except for the longer half-lives of $^3H$ and $^{14}C$), and are limited additionally by their lower sensitivity and by the susceptibility of the beta signals from these labels to quenching in the sample or liquid scintillation matrix used for counting of the label.

Many of these same limitations also apply to the use of other types of labels, particularly the problem that the magnitude of the signal from these nonradioactive labels tends to depend on the molecular environment of the label, including substances that are bound to the label covalently. Thus, it is generally important to minimize differences in the sample matrix (composition of background substances in the sample) when nonradioactive labels are being employed. This is not always controlled adequately, potentially leading to a loss in accuracy and precision of the analysis. However, it can be useful in certain analytical procedures that the signal from a label is sensitive to the molecular environment of the label, e.g., in fluorescence polarization ligand assays.

Another general limitation of currently available chemical labels is the loss in the assay sensitivity at some point when the sample of interest is progressively diluted to larger volumes prior to measurement of the signal associated with the label. This occurs because analytical procedures typically involve dilution steps arising from the addition of analytical reagents and solutions to the sample undergoing analysis, or from chromatographic separation steps, which generally, in the absence of enrichment mechanisms, cause dilution of the sample.

A particular shortcoming in the measurement of the class of labels called "electron absorbers", which are detected by their ability to absorb electrons in the vapor state, is that these labels have generally been employed only to measure molecules which are inherently volatile, or volatile after a labeling step. The most common technique for measuring molecules which contain electron absorbing groups as labels is gas chromatography with electron capture detection (GC-ECD) In this technique, the sample to be analyzed is first injected into a gas chromatography column. The components in the sample are then separated in the volatile state by passage through the column. Finally, these components are detected based on their ability to capture gaseous electrons which comprise or influence an electrical current in an electron capture detector located at the exit of the column.

Label or signal groups frequently are combined with reactivity groups in order to allow covalent attachment of the label to the substance of interest. For example, a Bolton Hunter reagent is available commercially in which a $^{125}I$ radiolabel is incorporated into a reactive molecule of p-hydroxyphenyl-propionic acid active ester. This reactive labeling reagent is used especially to radiolabel peptides and proteins with $^{125}I$.

The use of reactive, electron-absorbing labeling reagents in chemical analysis has been reviewed recently (Analytical Chemistry 52, 1002A (1980). These reagents are used to derivatize analytes to increase the sensitivity and volatility of the analytes for analysis by GC-ECD.

Label or signal groups have not been combined, however, with both reactivity and chemical release groups. These latter groups are defined as molecular groups which are specifically released by certain chemical reaction conditions to separate the signal group from the substance to which the labeling reagent has been attached. Two common examples of specific chemical release groups are methionylamides, which are split by cyanogen bromide; and 1,2-diol (vic-glycol) groups, which are split by periodate. The applications of methionylamide cleavage comprise generation of peptide fragments for sequencing (*Methods in Enzymology*, 11, 238 (1967)); removal of acylmethionine protecting groups in peptide synthesis (*Biochemistry* 13, 5159 (1974)), and *Biochemical Journal* 165, 479 (1977)); and polypeptide uncoupling in protein synthesis by recombinant DNA techniques (Science, 198 1056 (1977)).

A radiolabeled or otherwise labeled Edman reagent has been used to sequence polypeptides (see *J. Biol. Chem*, 250, 3629 (1975)); a process involving a release step. However, such Edman reagents do not incorporate a release group. The opportunity for release arises as a consequence of the attachment of the Edman reagent to a peptide or peptide equivalent. Splitting takes place at a site on the peptide near the attached Edman group, rather than within the attached Edman group. This applies as well to an Edman reagent which incorporates an electron absorbing group (*Proc. Soc. Exp. Biol. Med.*, 155, 287 (1977)).

A class of reagents called "protecting groups" are widely employed in peptide synthesis. These reagents are reactive, a few of them possess groups which can be detected, and these reagents ultimately are removed from the peptide after it is synthesized. However, protecting groups differ from release tags both functionally and structurally. The purpose of protecting groups is to facilitate synthesis rather than analysis, and their removal from the peptide, after this peptide is synthesized, necessarily involves a breakage of the bond previously made to the peptide by the reactivity group. Usually chemical cleavage is performed, but an enzyme-labile protecting group also has been used (*Proceedings National Academy of Sciences* 72, 2193 (1975)).

In one case a signal group (phenylazo residue) was incorporated into a protecting group for peptide synthesis, allowing one to monitor colorimetrically or visually the purification of the protecting group-peptide adduct (*Helv. Chim. Acta* 41, 491 (1958)), in German; summarized in English on pages 17-18 in "The Peptides" Vol 3 E. Gross and J. Meienhofer, Academic Press, 1981. However, this monitoring is performed without release of the signal group. Thus, one of the useful chemical conditions presented for removing the protecting group acceptably causes degradation and loss of color of the signal group.

A binding assay employing an enzyme-cleavable substrate as a label involving a conjugate compound has been introduced with the conjugate comprising the four-part structure "(galactosyl)-(umbelliferone)-(linking group)-(binding component)" (see U.S. Pat. Nos. 4,226,798 and 4,279,992). Enzymatic cleavage at the (galactosyl)-(umbelliferone) bond increases the intensity of the signal from the dye indicator umbelliferone group. However, there is no release of the umbelliferone signal group from the binding component, which binding component is the substance of interest.

SUMMARY OF THE INVENTION

My invention relates to a new class of analytical reagents called release tags and to the preparation and use of release tags in chemical analysis and to ketone signal compounds formed in the use of the reagents. My molecular release tag reagents are useful as chemical labels in analytical procedures particularly, but not necessarily in gas phase analysis.

My release tags comprise three molecular groups, "signal", "release", and "reactivity", such that the signal and reactivity groups are separated by the release group, as indicated here and have the general formula

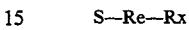

S—Re—Rx where S is the signal group, Re is the release tag to be attached covalently to a substance of interest, such as a ligand in a liquid medium, an analog thereof, or a specific binding partner thereof. The signal group is for detection purposes, comprising a molecular group or atom which can be detected with high sensitivity and specificity. The release group provides a site for specific chemical release. Splitting at this site releases the signal group from attachment to the substance of interest.

The reaction and release of a release tag compound with a substance of interest $S_I$ is illustrated by:

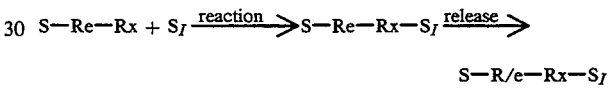

$$S-Re-Rx + S_I \xrightarrow{reaction} S-Re-Rx-S_I \xrightarrow{release}$$

$$S-R/e-Rx-S_I$$

where the release group is split, typically and preferably by a chemical reaction. The splitting of the release portion for the purpose of illustration only, is shown by a line between R and e of the Re group; however, splitting may take place at any selected place at the release group, e.g., within the release group, so that after splitting, fragments of the release group are with the signal and the reactivity group, or such that the release group is entirely with the signal or reactivity group. Fragments of the release group may also be lost in the splitting process.

My release tags are intended primarily to enhance the usefulness of nonradioactive labels in chemical analysis. Any of the chemical labels or signal groups of the prior art as set forth in the Background of the Invention can be used as the signal group in my release tags. In all of these cases, the ability to release specifically the signal group from the substance to which it is attached can lead to an enhanced opportunity to extract, purify, and/or concentrate this signal group prior to its measurement. The signal group therefore potentially can be detected with more accuracy and precision than if it remains attached to the substance of interest, due to the removal of the signal group from interferences prior to measurement of this signal group. Also, the signal group potentially can be detected with more sensitivity because of the concentration step.

Another advantage arising from the use of my release tag reagents in chemical analysis is the enhanced opportunity to employ structural analogs of a given type of signal or release group, giving rise to a series of analogous release tags. In this case the released signal groups will be separated, e.g., by a chromatographic step, prior to detection. For example, separation-detection can be provided by GC-ECD in the case of volatile electron-absorbing signal groups. Or, as a second example, high performance liquid chromatography (hplc) with fluorescent detection can be used to separate and quantitate analogous, fluorescent signal groups after release of these signal groups from the substance of interest. The several, closely related forms of the released signal group thereby can be measured essentially simultaneously and with comparable sensitivity and complete discrimination. A single separation-detection process and set of conditions then can be used to measure a given set of homologous release tags (usually differing only in the structures of their signal or release groups) irrespective of the nature of the substances to which these release tags are attached. This advantage of a universal separation-detection step for the analysis of a wide variety of substances labeled with a given set of homologous release tags applies as well to measurements carried out even with a single release tag, as long as these labeled substances are separated prior to measurement.

In the particular case of a release tag in which the released signal group is inherently volatile, or can be made so by a suitable derivatization procedure, then the use of such a release tag affords the additional advantage that separation-detection techniques like GC-ECD are extended to the analysis of nonvolatile substances. A related, potential advantage is also realized when the released signal group can be extracted into an organic solvent. In this case, the released signal group potentially can be isolated from an aqueous sample by extraction with an immiscible, highly volatile organic solvent, and then readily concentrated by evaporation. Whenever the released signal group can be extracted in this or an analogous manner, but the release tag analyte conjugate is not extractable, then appropriate pre-extraction of the sample being analyzed, prior to chemical release of the signal group, can be used to remove extractable interferences before the signal group is released and extracted. Ion-pair extractions, solid phase extractions, gas phase extractions, etc., are all relevant procedures.

Finally in the particular case of a release tag in which the released signal group is inherently volatile, and also is a highly electron-absorbing group, then the opportunity exists for ultrasensitive analysis with the use of such a release tag in conjunction with separation-detection by GC-ECD. For example, we have observed a detection limit of 90 attograms ($1.6 \times 10^{-19}$ mole) when the highly electron-absorbing compound N-N-dipentafluorobenzoyl-pentafluoroaniline is analyzed by GC-ECD.

As one illustrative example of the release tags of my invention, I have synthesized N-pentafluorobenzoyimethionyl-glycine-N-hydroxysuccinimide ester (N-PFB-Met-GLY-NHS) the structural formula of which is

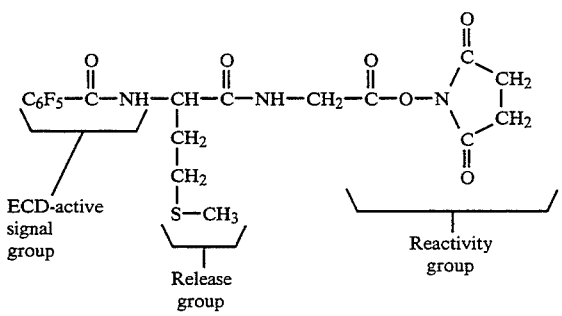

In this release tag, the signal group is N-PFB (sensitive by GC-ECD), the release group is methionylamide (susceptible to specific chemical release by cyanogen bromide, releasing the signal group as a nonpolar and volatile N-PFE-homoserine lactone), and the reactivity group is NHS (reacts especially with primary amino groups). The structural fomula of the released lactone signal group is:

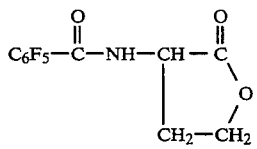

In an illustrative example of the use of this release tag, the release tag is used to analyze the hormone, thyroxine ($T_4$), in serum. The $T_4$ is purified by ion exchange chromatography. The $T_4$ analogue, 3', 5'-dibromo-3,5-diiodothyronine (($Br_2T_2$) is added as an internal standard. The $T_4$ and $Br_2T_2$ products are separated by high performance liquid chromatography and collected. The signal group is released from these two products by means of reaction with cyanogen bromide, and then quantitated by GC-ECD. The resulting quantitative value for $T_4$ agrees with that obtained by radioimmunoassay. Corresponding analysis of a hypothyroid serum, and of a serum blank containing no $T_4$, give results establishing control of interferences.

Other choices of signal groups/signal analysis methods besides N-PFB/GC-ECD include, but are not limited to: N-heptafluorobutyrl or N-p-(pentafluorophenoxy)-2, 3, 5, 6-tetrafluorobenzoyl or pentachlorophenyl/GC-ECD or negative chemical ionization mass spectrometry; fluorescein or rhodamine or dansyl or umbelliferyl or o-phthalyl/± liquid chromatography (LC) with fluorescence (or laser fluorescence) detection; N-3,5-dinitrobenzoyl or 4-N,N-dimethylazobenzene/± LC with absorbance detection; luminol or isoluminol/± LC with atomic absorption detection; nitroxide/± LC with electron spin resonance detection; $^3$H-acetyl or $^{35}$S-phenylthiocarbamate or $^{125}$I-Bolton Hunter Reagent/± LC with radioactivity detection; N-nitrosodiphenylamine or alkylnitrite or arylnitrite/± LC or ± GC with thermal energy analysis or pyrolysis-resonance ionization spectroscopy detection; and nicotinamide adenine dinucleotide coenzyme/± LC with dehydrogenase enzyme reaction and fluorescence or absorbance or visual detection.

Other choices of specific chemical release groups/specific chemical reaction release conditions include, but are not limited to, 1,2-diol/periodate; disulfide/mercaptoethanol; tryptophan or tyrosine/o-iodosobenzoic acid; thioester/hydroxylamine: azo group/sodium hydrosulfite; p-toluenesulfonic ester of a βγ-acetylenic alcohol/sodium iodide; olefin/ozone; benzyl ether/catalytic hydrogenation; alkyl, phenyl ether/hydrobromic acid; hydrazone/acetylacetone; thioether/cyanogen bromide benzylether/hydrogenolysis; benzyloxycarbonylamine/hydrogenation; alkyl- or arylsulfonylethyloxycarbonylamine/alkali; alkyl or arylthioethyl-oxycarbonylamine/oxidation-alkali; tosylamine/electrolytic reduction; S-benzylether/electrolytic reduction; O-nitrobenzylamide/photolysis 2-nitro-4,5-dimethoxy-benzyloxycarbonylamine/photolysis; amine oxide/pyrolysis (Cope elimination reaction); xanthate/pyrolysis (Chugaev reaction); and quaternary ammonium hydroxide/pyrolysis (Hofmann elimination reaction).

Other choices of reactivity groups include, but are not limited to, p-nitrophenyl ester, silyl halide, sulfonyl halide, acid halide, acid anhydride, α-bromo-ketone, α-iodo-ketone, dione, maleimide, diazonium, imido-ester, aldehyde, halonitrophenyl, arylazide, isothiocyanate, epoxide, carbene, nitrene, sulfenyl halide, amino and hydrazide. Further choices of signal group/signal analysis methods, reactivity groups and release groups would be apparent to those skilled in the art.

These reactivity groups collectively provide a wide variety of specific as well as general reactive sites, allowing release tags to be attached covalently to many kinds of substances to be quantitated, where such substances will each contain or can be provided with one or more functional groups capable of being reacted with the reactivity group on the release tag. Examples of such functional groups on substances to be quantitated, or functional groups which can be provided on this substance, are amino, carboxyl, hydroxy, guanidino, imidazole, thiol, phenol and aldehyde.

Examples of these release tag compounds other than N-PFB-Met-Gly-NHS are: (1) N-PFB-α-methyl-Met-Gly-NHS (which differs from the initial release only by substitution of a $CH_3$ in place of an H group in the release group part of the molecule, and thereby is useful for preparing an internal standard to be employed along with the use of N-PFB-Met-GLY-NHS); (2) N-Dansyl-Met-Gly-p-nitrophenyl ester (which illustrates the use of alternate signal and reactivity groups with the same release group as used initially, where the dansyl group is a fluorescent signal group); (3) N-3,5-Dinitrobenzoyl-Met-Gly-imido ester (which further illustrates alternative signal and reactivity groups with the same release group as used initially, where the dinitrobenzoyl group is an absorbance signal group); (4) N-PFB-Met(O)-Gly-NHS (which incorporates a methionine sulfoxide in place of a methionine group, which release tag comprises a tag in which the release group is more inert and protected from CNBr cleavage until the Met(O) group is chemically reduced to a Met group; (5) N-PFB-6-amino-4-methyl-3,4-dihydroxyhexanoic acid NHS ester (which illustrates the use of an alternate release group, i.e., a vic-diol release group, in combination with the same signal and reactivity groups as used initially); (6) p-Ferrocenylphenethyl (p-isothiocyanatobenzyl) (methyl) amine oxide (which illustrates a release tag with completely different signal, release and reactivity groups than used initially, where the ferrocenyl signal group is measured by atomic absorption, the phenethyl-amine oxide release group is released thermally by a Cope elimination reaction, and the isothiocyanatobenzyl group constitutes a reactivity group); and, (7) p-(4-Pentachlorophenoxy-benzyloxy)-phenylsulfonylchloride (which also illustrates a release tag with completely different signal, release and reactivity groups than used initially, where the pentachlorophenoxy group is electron absorbing, the benzyloxy release group is released by hydrogenolysis, and the phenylsulfonyl chloride part is a reactivity, group. A large number of release tag compounds can be defined based on the previous list of signal, release and reactivity groups, and from analogous signal, release and reactivity groups.

Examples of types of substances of interest which can be analyzed with the use of release tags are hormones, receptors, drugs, vitamins, haptens, particles, coenzymes, lipids, polysaccharides, sugars, prostaglandins, ecdysones, neurotransmitters, metabolites, enzymes, toxins, genes, DNA-carcinogen adducts, chemical biological warfare agents, poisons, nucleic acids, nucleotides, antibodies, proteins, enzyme substrates, pesticides, viruses, bacteria and smoke particles. Further examples of substances which can be analyzed with the use of release tags would be familiar to one skilled in the art.

In a preferred embodiment of my invention, the release tag reagent comprises a signal group, which on release provides or forms a stable ketone signal compound which may be detected in the chemical analytical technique used. The ketone signal compounds exhibit enhanced stability over the released aldehydic or lactone signal compounds. The signal group may comprise a halogen-containing group, such as a polyhalo like a polyfluoro group, which on release provides or forms a halogen-containing ketone compound. In particular, the release group to provide a ketone signal compound comprises a vic glycol group or an olefin group covalently bonded to the signal and reactivity groups of the release tag reagent. Many of the ketone signal groups are novel compounds which are usefully employed in the chemical analysis of the substance to be detected such as by gas or liquid phase techniques. For example, the ketone signal group may comprise a volatile compound subject to detection in the gas phase, e. g. by gas chromatography with electron capture detection.

The release group to provide a ketone signal compound has the formula:

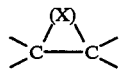

wherein X is selected from the group consisting of: two OH radicals; a covalent bond to form an olefin group; an oxygen atom to form an epoxide group; an NH group to form an alkylidenimine group; one OH and one $N(R)_2$ radical wherein R is a hydrogen or an alkyl radical or both; and an alkylidene-protected diol. The reactivity group may be an amino carboxyl ester group, while the signal group may be a halogen-containing group or wherein the signal group comprises a fluorescence group which on release forms a fluorescence ketone signal compound subject to detection by fluorescent detection techniques. The substance may have reactive groups selected from the group of OH radicals, $CO_2H$ radicals, SH radicals, phosphate radicals, carbonyl radicals, epoxy radicals, carbon radicals, hydrazide radicals, metal radicals, maleimide radicals, bromoalkyl radicals, iodoalkyl radicals, $NH_2$ radicals, and a NHR radical wherein R is an alkyl group or an aromatic group.

A release tag reagent suitable for use in the chemical analysis of a substance to be detected, which release tag reagent contains a vic glycol, ethylene, or epoxide release groups and has the formula:

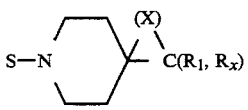

wherein S is a signal group which on release provides a signal piperidone ketone compound which may be detected in the chemical analysis technique employed for the detection of the substance; wherein $R_x$ is a reactivity group which is reactive with the reactive group of the substance to be detected; wherein $R_1$ is selected from the group consisting of hydrogen, an alkyl radical, and an aromatic radical and; wherein X is two OH radicals or a chemical bond or an alkylidene-protected diol. The signal group shown may comprise a halogen-containing signal group, while the reactivity group may include a covalently bonded carbonyl group to a carbon atom at $R_1$ containing the OH group. The reactivity group may have the formula $COR_2$ wherein $R_2$ is selected from the group of radicals consisting of: OH, alkoxyl, $NHCH_2CO_2$-alkyl ester, $NHCH_2$-acid radical and $NHCH_2CO$-N-hydroxysuccinimide.

One particular class of released novel electrophoric ketone signal compounds is represented by the formula:

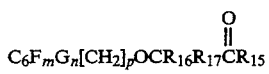

wherein m is a number 3 to 5, G is a hydrogen, alkyl, haloalkyl, halogen or alkoxy group, n is a number 1 to 2, $R_{15}$ is a alkyl group, p is a number from 0 to 1, and $R_{16}$ and $R_{17}$ are each a hydrogen or an alkyl group.

My release tag invention for diol, olefin, epoxide, alkylidenimine, amino-alcohol, hydroxy-keto, and amino-keto electrophoric release tags is illustrated by the following general formula such that the released signal group is an electrophoric ketone compound:

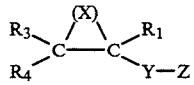

where $R_3$ and $R_4$ or both comprise an aromatic, aliphatic or alicyclic electrophore. Typically this electrophore comprises a mono- or poly-fluorinated organic group such as a polyfluorophenyl group such as a pentafluorophenyl group or a tetrafluorophenyl group or a methoxytetrafluorophenyl group, or a mono-, di-, tri-, tetra-,-penta-, hexa-, hepta-, octa-, nona-, deca-, undeca-, dodeca-, trideca-, tetradeca-, pentadeca-, hexadeca-, heptadeca-, nonadeca-, dideca-fluoro alkyl group, or a polyfluorinated aliphatic group such as a perfluoro $C_1$–$C_{12}$ alkyl group or preferably a perfluoro $C_3$ to $C_9$ perfluoroalkyl group such as a heptafluoropropyl group or a polyfluorinated alicyclic group such as a perfluoro $C_3$–$C_7$ alicyclic group, or a monohalogen or polyhalogen alkyl group, or a monohalogen or polyhalogen aromatic group, or a mono- or poly-nitro alkyl group, or a mono- or poly-nitro aromatic group, or a halogen-plus nitro-containing group. $R_3$ or $R_4$ or both may also compromise a polyfluoro alkyl-aromatic group or a polyfluoro alkyl-alicyclic group or a polyfluoro alicyclic-aromatic group. When only $R_3$ comprises an electrophore, then $R_4$ typically is an alkyl group such as a $C_1$ to $C_{12}$ alkyl group such as a methyl or a trideuteromoethyl group, or an alicyclic group such as a $C_3$ to $C_7$ alicyclic group, or an aromatic group such as a phenyl group, or an aliphatic-alicyclic group such as a methylcylopentyl group or an aliphatic-phenyl group such as a methylphenyl group or an alkoxy phenyl group such as a methoxyphenyl group. X is two hydroxy groups giving rise to a diol release group or X is a chemical bond giving rise to an olefin release group or X is an oxygen atom giving rise to an epoxide release group or X is an alkylidene-protected diol release group, or X is an amino group plus a hydroxy group giving rise to an amino-alcohol release group or X is an imine group (NH) giving rise to an alkylidenimine release group or, when $R_1$ is absent, X is a hydroxy or amino group plus a keto oxygen giving rise to a hydroxy-keto or amino-keto release group. $R_1$ is a hydrogen or an alkyl or an aromatic group or an alkyl-aromatic group. Y is a linking group such as a chemical bond or a carbonyl group or an alkyl group such as a $C_1$–$C_{12}$ alkyl group or an aromatic group. Z is a reactivity group such as a N-hydroxysuccinimide-glycyl group, or, when X is a bond or an oxygen or an alkylidene-protected diol, Z is an acid chloride group, or an alkyl carboxy group such as an acetoxy or an isobutyloxycarboxy group giving rise to anhydride or mixed anhydride reactivity group, or a bromoalkyl reactivity group or an iodoalkyl reactivity group such as a bromomethylketo group or an iodomethyl group or an iodoethyl group, or a reactive bromobenzyl group such as a bromobenzylamino group. Other reactivity groups for Z may comprise a hydrazide group, or a diazophenylamino group, or a hydroxymercuryphenylamino group, or a bromomethylketohydrazide group, or an amino alkylamino group such as an ethylenediamine group, or a maleimide group, or an imidazole group, or an epoxy group, or a dinitrofluorobenzene group, or an alkylimidate group, or an arylimidate group, or an azidophenyl group, or a glyoxal group, or an α-diketone group, or a thiocyanate group, or an alkoxy-methyl pyridinium group, or an arylalkoxymethyl pyridinium group, or a sulfonyl aziridine group, or an alkyl sulfate group, or an arlysulfonylalkoxyalkyl group, or an aldehyde group, or a triazine group or a sulfhydryl group or a carboxyl group or an amino group or a hydroxy group. When X is a bond or an oxygen or an alkylidene-protected diol, Z may also comprise a chlorosulfonylphenylamino group or a mustard group or a hydroxyalkylamino group, or an isocyanate group. Z may also react onto a metal side of a substance of interest, or provide a metal reactivity group. Z may also comprise a phosphorous- or boron- or silicon- containing reactivity group.

To further illustrate a release tag having a diol release group, I have synthesized the following compounds 1-6, and from these one can synthesize compounds 7-13, using these procedures and those reported in Example 1.

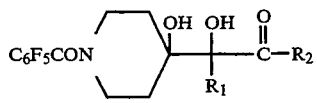

| | R₁ | R₂ |
|---|---|---|
| 1 | H | OCH₃ |
| 2 | CH₃ | OCH₃ |
| 3 | CH₃ | OCH₂CH₃ |
| 4 | H | OH |
| 5 | CH₃ | OH |
| 6 | H | NHCH₂CO₂CH₃ |
| 7 | CH₃ | NHCH₂CO₂CH₃ |
| 8 | H | NHCH₂CO₂H |
| 9 | CH₃ | NHCH₂CO₂H |
| 10 | H | NHCH₂CONHS |
| 11 | CH₃ | NHCH₂CONHS |
| 12 | H | NHCH₂CO-thyroxine |
| 13 | CH₃ | NHCH₂CO-thyroxine |

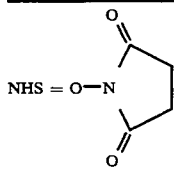

A diol release tag is attractive because it potentially can be cleaved rapidly and specifically under mile acqueous conditions employing sodium periodate. The mildness of these latter reaction conditions is indicated by the common use of sodium periodate to modify living cells involving analogous cleavage of diol containing sugar groups on the surfaces of these cells. Sodium periodate is also a non-toxic, inexpensive reagent that is soluble in both water and water-organic solvent solutions. This broad solubility range for sodium periodate guarantees that a diol release tag can be used under a broad variety of solvent conditions, giving it a wide spectrum of applications. For example, my diol release tag can be used to label many types of biological molecules having either aqueous or aqueous-organic solubility, including subsequent release of the signal group by a sodium periodate release reaction at the 1,2 diol site. The solubility range of the above diol compounds 1-13 is also enhanced by the diol structure contributing polarity for enhanced solubility under aqueous conditions, along with the presence of a nonpolar pentafluorobenzamide group immediately adjacent to the diol structure, enhancing the solubility under organic solubility conditions.

Compounds 1-7 are diol release tag precursors having a pentafluorobenzamide electrophoric signal group and a diol release group with an ester group, COR₂, that can be readily converted to many types of reactivity groups by conventional chemical reactions. For example, release tags 8 and 9 can be activated with a carbodiimide or carbonyldiimidazole in the presence of N-hydroxysuccinimide (NHS) to form release tags 10 and 11, having a pentafluorobenzamide signal groups, a diol release group, and an NHS ester reactivity group. Compounds 12 and 13 illustrate the attachment of release tags 10 and 11, respectively, onto the α- amino site of thyroxine. This reaction was illustrated by reacting the methionylamide release tag, having a corresponding NHS ester reactivity group, onto thyroxine in Example 1.

Release of compounds 1-13 at the diol group by sodium periodate to yield the corresponding released signal group N-(pentafluorobenzoyl)-4- piperidone, compound 14, occurs as follows;

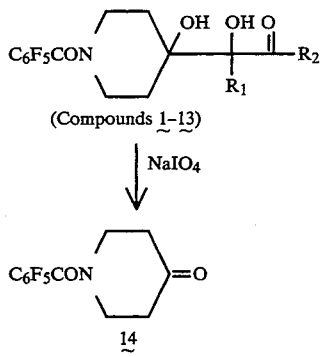

The released signal group 14, a ketone, has been quantitated by high performance liquid chromatography and preferably by gas chromatography with electron capture detection, since the pentafluorobenzoylamide moiety provides high sensitivity for detection by the latter technique.

In Table 1 is shown the rates of release of the ketone signal group 14 from the diol compounds 1-6 under various aqueous and aqueous-organic conditions. Importantly, quite rapid rates of release are seen for compounds 1, 4, 5 and 6 even at room temperature (23° C.). In the representative case of compound 1, it is seen that this rapid release persists under a variety of aqueous organic conditions, involving variations in organic cosolvent, pH, salt concentration and the presence of 7 M urea. For example, a kinetic value in this table of "10" corresponds to a rate constant of 0.1 or a half-life for the reaction of about 1 minute. The use of a higher temperature for the reaction can considerably increase the rate of cleavage, e.g. the 7-fold faster cleavage of compound 2 at 60° C. as opposed to 23° C.

To illustrate a release tag having an olefin release group, I have prepared compounds 15-18 from which the corresponding compounds 19-27 can be prepared by the procedures used to prepare compounds 1-13 and 15-18, and also the procedures used in example 1.

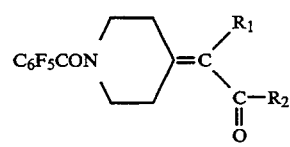

| | R₁ | R₂ |
|---|---|---|
| 15 | H | OCH₃ |
| 16 | CH₃ | OCH₃ |
| 17 | CH₃ | OCH₂CH₃ |
| 18 | H | OH |
| 19 | CH₃ | OH |
| 20 | H | NHCH₂CO₂CH₃ |
| 21 | CH₃ | NHCH₂CO₂CH₃ |
| 22 | H | NHCH₂CO₂H |

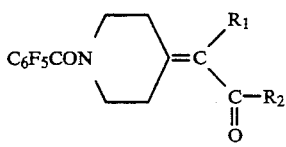

| | R₁ | R₂ |
|---|---|---|
| 23 | CH₃ | NHCH₂CO₂H |
| 24 | H | NHCH₂CONHS |
| 25 | CH₃ | NHCH₂CONHS |
| 26 | H | NHCH₂CO-thyroxine |
| 27 | CH₃ | NHCH₂CO-thyroxine |

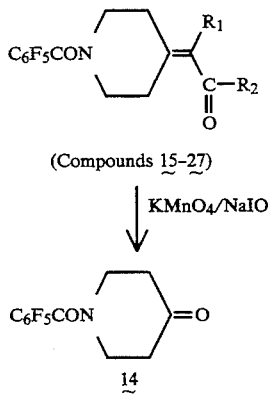

Olefin release tags are attractive not only because they can be specifically released under aqueous and also organic-aqueous conditions with potassium permanganate/sodium periodate, but also because the inertness of the olefin group comprising a carbon-carbon double bond facilitates their synthesis and allows a wide variety of reactivity groups to be incorporated into these molecules. The small, uniform structural features of these compounds also should aid their synthesis and general ease of use. This incudes their use as conventional electrophoric tags forming volatile derivatives of some analytes where these derivatives can be analyzed directly, or after further derivatization, by gas chromatography with electron capture detection or detection with negative ion chemical ionization mass spectrometry.

The release of compounds 15-17 by potassium permanganate/sodium periodate to give the corresponding N-(pentafluorobenzoyl)-4-piperidone compound 14 is shown below. Compound 14 is the same ketone compound that is released by sodium periodate treatment of the corresponding diol compounds 1-13.

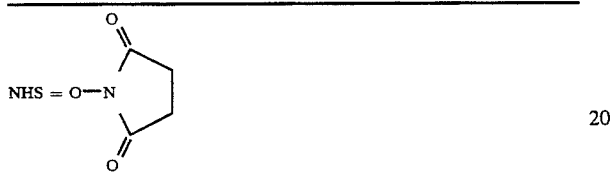

(Compounds 15-27)

↓ KMnO₄/NaIO₄

C₆F₅CON⟨⟩=O

14

To illustrate multiplicity for the electrophoric signal group in a release tag, I have synthesized compound 28, having a p-methoxy-tetrafluorobenzamide electrophore, from which the released signal group 29 can be synthesized using the procedures reported in examples 1 and 2, where R₅ is a C₁-C₁₂ alkyl and preferably a C₁-C₆ alkyl group or a C₃-C₇ alicyclic group or an alkylalicyclic group. For example, isomeric alkyl groups such as propyl and isopropyl may be used for R₅. To illustrate this, I have synthesized compound 29 where R₅ is methyl.

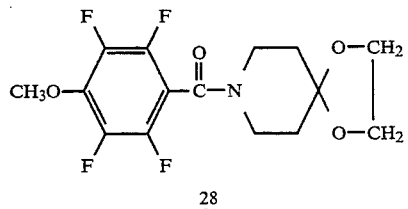

28

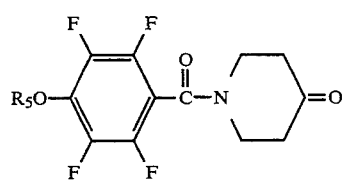

29 (R₅ = alkyl)

From compound 29, release tags can be prepared using the same methods used to prepare release tags 10, 11, 24, and 25, relying especially on a Wittig reaction.

To further illustrate an electrophoric olefin release tag, I have synthesized a halogen-containing acetophenone ketone signal compound 30a, and from this I have synthesized compound 30b, a release tag precursor having a p-(N-methyl-N-pentafluorobenzoyl-amino)-phenyl electrophoric signal group, an olefin release group, and a methyl carboxylic ester group. This allows one to synthesize release tag compounds 31 using the procedures reported for 1-29 and in example 1.

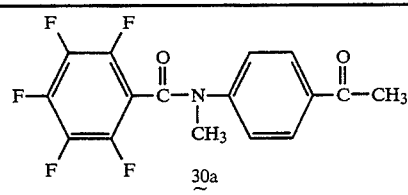

30a

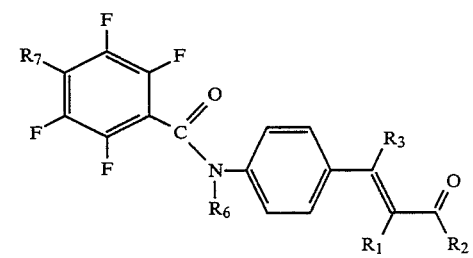

| Compound | R₇ | R₆ | R₃ | R₂ | R₁ |
|---|---|---|---|---|---|
| 30b | F | CH₃ | CH₃ | OCH₃ | H |
| 31 | F or alkoxy | alkyl | alkyl | Cl, NHS, NHCH₂CONHS, or another reactivity group | H or alkyl |

In release tag 31, Y is a chemical bond and Z is COR₂. R₇ may also be substituted ortho or meta on the tetrafluorophenyl ring. I have also synthesized the halophenyl alkanone ketone signal groups 32 and 33 from which release tags can be prepared using the same methods used to prepare release tags from signal compound 29, including the methods used to prepare release tags 10, 11, 24 and 25.

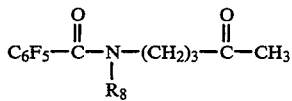

32  $R_8 = H$
33  $R_8 = COC_6F_5$.

I have also synthesized the halophenyl alkanophenone signal group 34 from which release tags can be prepared using the same methods used to prepare release tags from signal compound 29, including the methods used to prepare release tags 10, 11, 24, and 25.

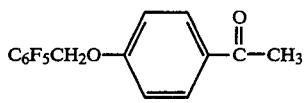

34

This allows one to prepare the following signal groups 35 using the same methods used to prepare signal groups 28, 29, and 34, from which release tags can be prepared using the same methods used to prepare release tags from signal compound 29, including methods used to prepare release tags 10, 11, 24, and 25.

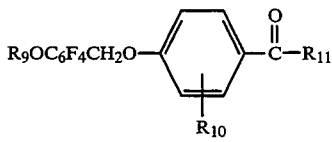

35  ($R_9, R_{10}, R_{11}$ = alkyl)

The group $R_9O$ may be substituted at ortho, meta or para positions on the tetrafluorophenyl ring, or may be di- or tri- substituted on this ring.

I have also synthesized the fluorine-containing alkanone signal group 36, and the fluoroalkoxyphenyl alkanophenones 37 and 38 from which release tags can be prepared using the same methods used to prepare release tags from signal compound 29, including the methods used to prepare release tags 10, 11, 24 and 25.

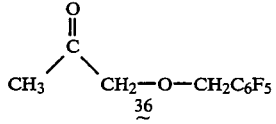

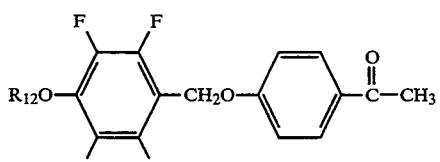

37  $R_{12}$ = propyl

38  $R_{12}$ = isopropyl

The $R_{12}O$ group may also be ortho or meta substituted on the tetrafluorophenyl ring, or may be di- or tri-substituted on this ring. I have also synthesized the α-halophenoxy alkanone signal group 39, pentafluorophenoxyacetone.

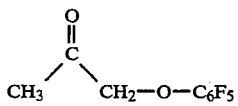

39

Using the methods employed to synthesize signal groups 36 and 39, one can also synthesize signal groups 40 and 41 from which release tags can be prepared using the same methods using to prepare release tags from signal compound 29, including the methods used to prepare release tags 10, 11, 24 and 25, where $R_{13}$ and $R_{14}$ comprise an electrophore, $R_{15}$ comprises an alkyl or an aromatic group or an electrophore, $Q_1$ and $Q_2$ comprise an oxygen, nitrogen, sulfur or selenium atom, and $R_{16}$–$R_{19}$ comprise hydrogen, alkyl, alkylidene, or aromatic groups, or electrophores, or halogen atoms, or mixtures of these, such as two hydrogens, a hydrogen and an alkyl group, two alkyl groups, a hydrogen and an aromatic group, an alkyl and an aromatic groups, or two aromatic groups. For example, $R_{15}$ may be $CF_3$ or $CF_2H$ or $CFH_2$, $R_{16}$–$R_{19}$ may be two hydrogens, $Q_1$ may be an oxygen atom, and $R_{13}$ may be $CH_2C_6F_4OCH_3$ or $CH_2C_6F_4OCD_3$ or $C_rF_{r+2}$ where r is 1 to 8.

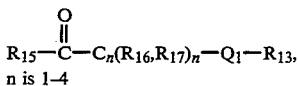

40 n is 1–4

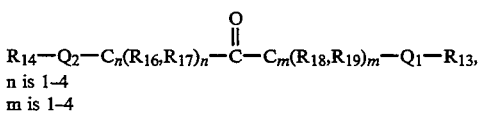

41 n is 1–4
m is 1–4

To further illustrate an electrophoric olefin release tag, I have synthesized compounds 42 and 43, fluorophenyl cinnamoyl olefin release tag precursors.

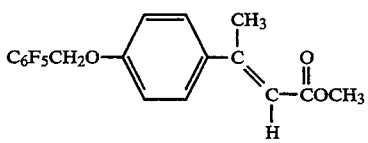

42

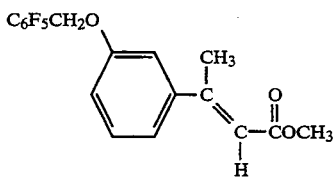

43

One can also release an electrophoric ketone signal group by an elimination reaction on an O-C-H elimination group, as by a thermal, electrophilic, nucleophilic or combined process, as follows:

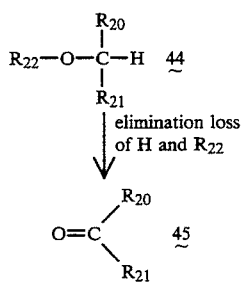

44 elimination loss
of H and $R_{22}$

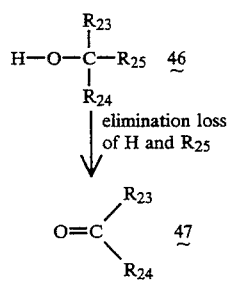

45 where $R_{20}$ or $R_{21}$ or both are electrophoric, and $R_{22}$ comprises a reactivity group or the subsequent covalent linking group that forms when 44 is covalently reacted onto a substance of interest. Similarly, a thioketone or selenoketone signal compound may be generated. Also a ketone signal compound generated by primary cleavage of a vic-glycol or olefin group may undergo secondary elimination cleavage to yield a subsequent ketone signal compound.

One can also release an electrophoric ketone signal group by an elimination reaction on an H-O-C elimination group, as by thermal, electrophilic, nucleophilic or combined process, as follows:

$$H-O-\underset{\underset{R_{24}}{|}}{\overset{\overset{R_{23}}{|}}{C}}-R_{25} \quad 46$$

elimination loss
of H and $R_{25}$ $$O=C\diagup\overset{R_{23}}{\underset{R_{24}}{\diagdown}} \quad 47$$

where $R_{23}$ or $R_{24}$ or both are electrophoric, and $R_{25}$ comprises a reactivity group or the subsequent covalent linking group that forms when 46 is covalently reacted onto a substance of interest. For example, β-hydroxy ketones, β-hydroxy olefins, β-hydroxy alkynes and β-hydroxy esters can be thermally decomposed to form ketones (B. L. Yates and J. Quijano, *J. Org. Chem.* 34, 2506, 1969, R. T. Arnold and G. Smolinsky, *J. Am. Chem. Soc.* 81, 6443, 1959, B. L. Yates, A. Ramirez and O. Velasquez, *J. Org. Chem.* 36, 3379, 1971, and refferences cited therein), hereby incorporated by referrence. Similarly, a thioketone or selenoketone signal compound may be generated.

Released an O-C-H or an H-O-C eliminated group to give an electrophoric ketone may take place not only as part of sample pretreatment prior to injection into a gas chromatograph, but may take place within the gas chromatograph, e.g. in the injection port. This includes the injection of release tag-labeled macromoiecules and macrosubstances such as release tag-labeled -antibodies. -proteins, -peptides, -nucleic acids, -polynucleotides, -polysaccharides, -complex lipids, -bacteria, -viruses, -cells, -synthetic polymers, -particles, -related substances and combinations thereof.

I have also synthesized the halogen-containing olefin cinnamyl release tag 48, m-pentafluorobenzyloxy-β-methyl-cinnamic acid, and 49, m-pentafluorobenzyloxy-β-methyl -cinnamoyl chloride.

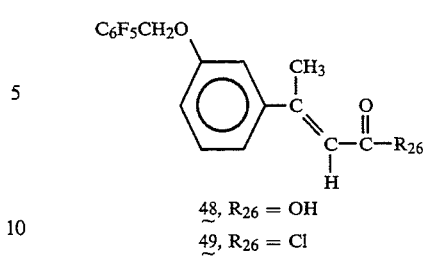

48, $R_{26}$ = OH
49, $R_{26}$ = Cl

One can also use some of my release tags as direct electrophore labels, ie, that the release tag-compound covalent conjugate is directly analyzed by gas chromatography without any release of the signal group prior to injection into the gas chromatograph.

One can also employ my novel electrophoric ketone signal groups as direct electrophore labels by giving them a reactive group so that the ketone electrophore-compound (or analogous ketone-derived methoxime-electrophoric-compound) covalent conjugate can be formed and analyzed directly by gas chromatography, For example, one can synthesize the electrophoric ketone alkylating agent 50, 1-bromo-3-pentafluorophenoxy-acetone, that combines an β-(fluorophenoxy)-alkanone novel electrophore with a conventional β-(-bromomethylketo reactivity group. One can also prepare compound 51 having a hydroxy reactivity group.

$$R_{27}-CH_2-\overset{\overset{O}{\|}}{C}-CH_2-O-C_6F_5$$

50, $R_{27}$ = Br
51, $R_{27}$ = OH

One can also prepare compound 52, an electrophoric silylating reagent also having good GC-ECD properties in which the keto group is converted into a methoxime group, allowing a silyl chloride reactivity group to be present.

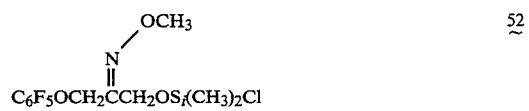

52

One can also prepare compound 53, having an α-bromomethylketo reactivity group, where the pentafluorobenzyloxy substituent may also be substituted meta or ortho.

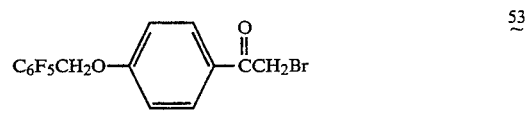

53

One can also prepare compound 54, an α-(fluoroalkoxyphenoxy)-alkanone, that can also be converted to direct electrophore labels.

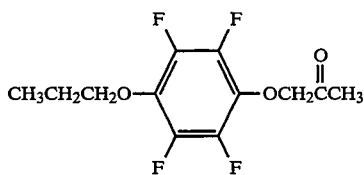

54

It is significant and novel that I have prepared 1,2-glyco and olefin release groups that release a signal ketone as opposed to a signal aldehyde compound upon cleavage with periodate and permanganate/periodate, respectively. Aldehydes tend to be reactive, unstable compounds. It is therefore not desirable for the purposes of release tags to release an aldehyde signal compound. In contrast, ketones are relatively unreactive and stable compounds, suitable for the purposes of release tags, especially gas phase detection. It is therefore important that I have incorporated special structural features into my 1,2-glycol and olefin release tags, and defined these features for H-O-C and O-C-H elimination group release tags, in order to obtain and release a ketone as opposed to an aldehyde signal compound.

One can also incorporate other signal groups such as fluorophores, lumiphores, radioisotopes, coenzynes, enzymes, electrochemiphores (such as nitro-containing compounds, for electrochemical detection) dyes or organometallics into my ketone release tags. Nitro-containing compounds also are electrophores allowing their detection by ECD.

One can also release an electrophoric ketone signal group by an elimination reaction on an -O-C-O-C(=O)-elimination group, as by a thermal, electrophilic, nucleophilic or combined process, as follows:

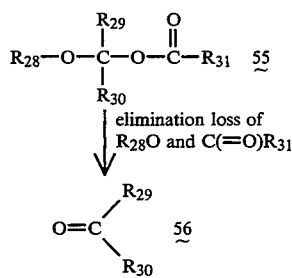

where $R_{28}$ is an alkyl or aryl group, $R_{29}$ or $R_{30}$ or both are electrophoric, and $R_{31}$ comprises a reactivity group or the subsequent covalent linking group that forms when 55 is covalently reacted onto a substance of interest. For example, Newallis and Lombardo (*J. Org. Chem.* 30, 3834, 1965) hereby incorporated by reference, have synthesized several fluoroacetone hemiketal esters and carbonates that can be pyrolyzed to the corresponding fluoroacetones. Similarly, a thioketone or selenoketone signal compound may be generated. For example, one can prepare release tag 57.

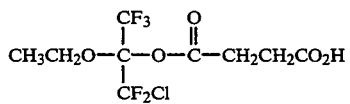

It is novel to employ alkyl structural isomers of electrophores as signal groups in chemical analysis, for example the propyl and isopropyl isomers 37 and 38. This will be particularly useful for internal standardization purposes, since it will allow an electrophore (direct or release tag)-labeled substance to be monitored closely by the corresponding electrophore'-labeled substance, where electrophore and electrophore' are structural isomers. This close monitoring will continue in the GC-ECD, yet the GC-ECD will discriminate these isomers. I have demonstrated this GC-ECD capability with compounds 37 and 38.

One can also prepare the following alkyl isomeric electrophores to provide an alternate synthetic route to ketone compounds 37 and 38, or to serve as novel, isomeric direct electrophores.

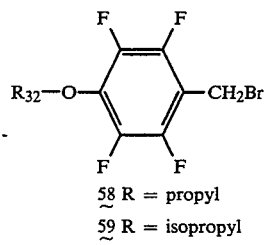

58 R = propyl
59 R = isopropyl

One can also prepare the following alkyl isomeric ketone electrophores from which release tags can be prepared using the same methods used to prepare release tags from signal compound 29, including the methods used to prepare release tags 10, 11, 24, and 25.

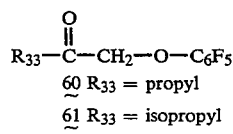

60 $R_{33}$ = propyl
61 $R_{33}$ = isopropyl

DESCRIPTION OF THE EMBODIMENTS

Apparatus

All $^1$H NMR experiments were performed on a Varian T-60A instrument. The chemical shift data were reported in parts per million (δ) relative to tetramethylsilane (O).

Infrared spectra were taken on Perkin-Elmer Model X99 spectrophotometer and the absorptions are reported in wave numbers (cm$^{-1}$). Mass spectra were obtained on a Nuclide 12-90-G instrument. Melting points were determined on a Thomas-Hoover capillary melting point apparatus and are uncorrected. High performance liquid chromatography was done with a C8-Supelcosil column, 15 cm×4.6 mm, particle diameter 5 μm, using UV monitoring at 254 nm.

N-(Pentafluorobenzoyl)-4-piperidone ethylene ketal, A

4-Piperidone ethylene ketal (2.04 g, 14.5 mmol) was dissolved in dry CH$_3$CN (50 ml). Et$_3$N (3 ml) was added, the reaction was cooled to 0° C. Pentafluorobenzoyl chloride (3.36 g, 14.5 mmol) was added dropwise with stirring, and the temperature was kept between 0°-5° C. during the addition. The reaction mixture was stirred at room temperature for 15 min, and then it was diluted with ethyl acetate (60 ml). The organic layer was washed with 10% HCl, 10% NaHCO$_3$, and H$_2$O, followed by drying over anhydrous Na$_2$SO$_4$. Evaporation afforded a white solid which was recrystallized from hexane/acetone to yield colorless crystals of compound 3 (4.7 g, 97%); m.p. 99°–101° C. IR (film): 2960, 1820, 1660 and 1510 cm$^{-1}$; $^1$H NMR (CDCl$_3$): δ 1.80 (overlap of two t, 4H, 2 CH$_2$ adjacent to the ketal), δ 3.42 and 3.92 (t, 4H, 2 CH$_2$ adjacent to the nitrogen), and δ 4.00 (s, 4H, ethylene ketal); MS: m/z 343 (M+), 195 and 167.

N-(Pentafluorobenzoyl)-4-piperidone, 14

A solution of compound A (4.7 g, 13.7 mmol) in dioxane (50 ml) was treated with a mixture of conc HCl and HClO$_4$ (12 ml, 1:1 ratio). The reaction mixture was refluxed for 4 hr. Ethyl acetate was added to the reaction mixture, and the organic layer was washed with 10% NaHCO$_3$ and H$_2$O and dried over anhydrous Na$_2$SO$_4$. Evaporation of the solvent afforded a white solid which was 2 spots on TLC (3:7 ethyl acetate/hexane). Flash chromatography on silica gel (3:7 ethyl acetate/hexane) yielded the piperidone derivative 2 (3.4 g, 85%), mp 124°–125° C. IR (film): 1740 and 1650 cm$^{-1}$; $^1$H NMR (CDCl$_3$): δ 2.53 (overlap of two t of 2 CH$_2$ adjacent to the carbonyl), δ 3.63 and 4.03 (two t, 2 CH$_2$ adjacent to the nitrogen); MS: m/z 293 (M+), 195 and 167.

Methyl [N-(pentafluorobenzoyl)-4-piperidylidenyl]-acetate, 15

A mixture of the piperidone derivative 14 (2.93 g, 10 mmol) and methyl(triphenylphosphoranylidene)acetate (3.34 g, 1 mmol) in xylene (100 mL) was refluxed under nitrogen for 3 hr. Evaporation of the solvent under vacuum afforded a dark yellow solid which was purified by flash chromatography (3:7 ethyl acetate/hexane) to yield a white solid (3.35 g, 96%); mp 112°–113° C.; IR (film): 2990, 2930, 1705, 1650 and 1620 cm$^{-1}$; $^1$H NMR (CDCl$_3$): δ 2.43 (t, 2H, CH$_2$ trans to the carboxylic ester), 3.05 (t, 2H, CH$_2$ cis to the carboxylic ester), 3.63 (s, 3H, methyl ester), 3.40 and 3.82 (two t, 4H, 2 CH$_2$ adjacent to the N) and 5.7 (br s, 1H, vinylic proton); MS: m/z 349 (M+), 318, 290, 195 and 167.

Methyl [N-(pentafluorobenzoyl)-4-piperidylidenyl]-acetate-glycol, 1

The α-β-unsaturated ester, 15(1.25 g, 3.58 mmol) was hydroxylated with osmium tetroxide (1.0 g, 3.91 mmol) and pyridine (5 ml) in dry tetrahydrofuran (26 ml). The reaction mixture was stirred under N$_2$ at room temperature for 3 hr. A solution of 10% sodium bisulfite (30 ml) was added, and the reaction mixture was stirred vigorously for 90 min. Ethyl acetate was added, and the aqueous layer was extracted 4 times with ethyl acetate. The combined organic extracts were washed with 10% HCl, 10% NaHCO$_3$ and H$_2$O, and then dried over anhydrous Na$_2$SO$_4$. Evaporation of the solvent afforded a white solid that was recrystallized from methanol/hexane to yield colorless needles (1.27 g, 92%), one spot on TLC (1:1 ethyl acetate/hexane); mp 115°–11/° C.; IR (KBr): 3480, 3270, 1730 and 1640 cm$^{-1}$; $^1$H NMR (CDCl$_3$): δ 1.77 (br m, 4H, 2 CH$_2$ adjacent to the glycol), 3.37 and 3.87 (br m, 4H, 2 CH$_2$ adjacent to the N) , 3.72 (s, 3H, CH$_3$ ester overlapped with CH$_2$ at 3.87), 4.37 and 4.58 (br s, 2H, 2 OH of the glycol); MS: m/z 383 (M+), 294, 195 and 167.

[N-(pentafluorobenzoyl)-4-piperidylidenyl]-acetic acid glycol, 4

The ester-glycol 1 (1.047 g, 2.7 mmol) was dissolved in methanol (15 ml), and aqueous NaOH (20.5 ml, 0.2 N) was added. The reaction mixture was refluxed for 30 min and adjusted to pH 3 with 10% HCl. The solution was extracted 5 times with ethyl acetate and the combined organic extract was washed with water and then dried over anhydrous Na$_2$SO$_4$. Evaporation afforded a white solid (955 mg, 99%), that was a single spot on TLC (1:9 methanol/ethyl acetate). Recrystallization from methanol yielded colorless crystals, mp 295°–299° C.; IR (KBr): 3400, 2920, 1720 and 1635 cm$^{-1}$; $^1$H NMR (DMSO-d$_6$): δ 1.65 (br m, 4H, 2 CH$_2$ adjacent to the glycol), 3.28 and 2.70 (br m, 4H, 2 CH$_2$ adjacent to the N), 4.13 and 4.33 (br s, 2H, 2 OH of the glycol), and 5.50 (br s, 1H, COOH, disappeared by addition of D$_2$O); MS: m/z 369 (M+), 306, 294, 195 and 167.

Methyl 2'-[N-(pentafluorobenzoyl)-4-piperidylidenyl]-propionate, 16

A mixture of the piperidone derivative, 14 (2 g, 6.8 mmol) and methyl 2-(triphenylphosphoranylidene)propionate (2.37 g, 6.8 mmol) in xylene (120 ml) was refluxed for 48 hours. Evaporation of the solvent under vacuum afforded a yellow solid, which was purified by flash chromatography (2:8 ethyl acetate/hexane) to yield a white solid, which was recrystallized from ether; (1.6 g, 65%); mp 91°–92° C.; IR (KBr): 2950, 2870, 1715 and 1650 cm$^{-1}$; $^1$H NMR (CDCl$_3$): δ 1.98 (br, m, 3H, alkyl CH$_3$), 2.69 (br, t, 4H, 2 CH$_2$ adjacent to the double bond), 3.40 and 3.80 (br, two t, 4H, 2 CH$_2$ adjacent to the nitrogen) 3.75 (s, 3H, methyl ester, overlapped with CH$_2$ at 3.80); MS: m/z 363 (M+), 332, 331, 304, 303, 195 and 167.

Methyl 2'-[N-(pentafluorobenzoyl)-4-peperidylidenyl]-propionate glycol, 2

This procedure starting with 16 was the same as that used to convert 15 to 1 except that evaporation of the solvent after drying with Na$_2$SO$_4$ afforded a colorless oil which showed 2 spots on silica TLC (5:5 EtOAC/hexane). The glycol was separated from unreacted olefin by flash chromatography on silica gel (5:5 ethyl acetate/hexane) to yield a white solid (730 mg, 83%); mp 123°–124° C.; IR (KBr): 3500, 3340, 2990, 2950, 2920, 1735 and 1655 cm$^{-1}$; $^1$H NMR (CDCl$_3$): δ 1.42 (s, 3H, alkyl CH$_3$), 1.74 (br, m, 4H, 2 CH$_2$ adjacent to the glycol), 3.4 (br, m, 4H, 2 CH$_2$ adjacent to the nitrogen), 3.88 (s, 3H, methyl ester), 4.59 and 4.78 (br, two s, 2H, 2 OH of the glycol); MS: m/z 397 (M+), 338, 320, 294, 195 and 167.

2'-[N-(pentafluorobenzoyl)-4-piperidylidenyl]-propionic acid glycol, 5

This procedure, starting with 2 was the same as that used to convert 1 to 4. The white solid product was recrystallized from methanol/chloroform to yield colorless crystals (290 mg, 88%); mp 174° C.; IR (KBr): 3440, 2990, 2940, 1730 and 1650 cm$^{-1}$; $^1$H NMR (DMSO-d$_6$): δ 1.24 (s, 3H, alkyl CH$_3$), 1.7 (br, m, 4H, 2 CH$_2$ adjacent to the glycol, 3.41 (br, m, 4H, 2 CH$_2$ adjacent to the N), 4.36 and 4.58 (br, s, 2H, 2 OH of the glycol overlapped with the COOH at 4.74), 4.74 (br, s, COOH, disappeared by addition of D$_2$O); MS: m/z 338, 320, 306, 195, 167 and 90.

{[N-(pentafluorobenzoyl)-4-piperidylidenyl]-acetyl}-glycine methyl ester glycol, 6

The acid glycol, 4 (110 mg, 0.3 mmol) was suspended in chloroform (3 ml) and glycine methyl ester hydrochloride (188 mg, 1.5 mmol) and triethylamine (152 mg, 1.5 mmol) in chloroform (1.5 ml) were added. 1-Hydroxybenzotriazole (40 mg, 0.3 mmol) was added and the reaction mixture was cooled to 0° C. Dicyclohexylcarbodiimide (62 mg, 0.3 mmol) was added and the reaction mixture was stirred at room temperature for 24 h. The product was separated from dicyclohexylurea and 1-hydroxybenzotriazole as well as unreacted acid by flash chromatography (9:1 ethylacetate/hexane) to yield a white solid (30 mg, 25%); IR (KBr): 3400, 3320, 2960, 1740, 1650 cm$^{-1}$; MS: m/z 409, 315, 306, 294, 195, 167 and 147.

Ethyl 2'-[N-(pentafluorobenzoyl)-4-piperidyidenyl]-propionate, 17

A mixture of the piperidone derivative, 14 (1.75 g, 5.96 mmol) and ethyl 2-(triphenylphosphoranylidene) propionate (2.1 g, 5.96 mmol) in xylene (70 ml) was refluxed under nitrogen for 72 h. Evaporation of the solvent under vacuum afforded a allow oil which was purified by flash chromatography (3:7 ethyl acetate/hexane) to give a white solid (1.2 g, 53%); IR (film): 2980, 2925, 2865, 1710, and 1660 cm$^{-1}$; $^1$H NMR (CDCl$_3$): δ 1.28 (t, 3H, CH$_3$ of ethyl ester), 1.94 (m, 3H, olefinic CH$_3$), 2.61 (br, t, 4H, 2 CH$_2$ adjacent to olefinic carbon), 3.40 and 3.78 (br, two t, 4H, 2 CH$_2$ adjacent to nitrogen), 4.24 (q, 2H, CH$_2$ of ethylester); MS: 377 (M$^+$), 348, 332, 331, 304, 303, 195 and 167.

Ethyl 2'-[N-(pentafluorobenzoyl)-4-piperidylidenyl]-propionate glycol, 3

The olefin 17 (1.2 g, 3.18 mmol) was dissolved in t-butanol (27 ml) ice (9 g) and acetone (3 ml) were added and the solution was cooled to 0° C. A solution of KMnO$_4$ (1.0 g, 6.36 mmol) and NaOH (254 mg, 6.36 mmol) in H$_2$O (35 ml) was cooled to 0° C. and added slowly. A solution of 10% sodium bisulfite (30 ml) was added after 5 min and the reaction mixture was stirred for another 5 min. The aqueous layer was extracted 4 times with CHCl$_3$. The organic extracts were washed with H$_2$O and dried over anhydrous Na$_2$SO$_4$. Evaporation of the solvent afforded a slightly brown solid (1.19 g, 91%) which was recrystallized from ether to give white crystals; mp 125°-126° C.; IR (film): 3520, 3440, 3000, 2990, 2920, 1730, 1665 cm$^{-1}$; $^1$H NMR (CDCl$_3$); δ 1.34 (t, 3H, CH$_3$ of the ethyl ester), 1.42 (s, 3H, alkyl CH$_3$ overlapped with the CH$_3$ of the ester), 1.73 (br, m, 4H, 2 CH$_2$ adjacent to the glycol), 3.31 (br, m, 4H, 2 CH$_2$ adjacent to the nitrogen), 4.34 (q, 2H, CH$_2$ of the ethyl ester), 4.54 and 4.78 (br, two s, 2H, 2 OH of the glycol, the 4.54 overlapped with the CH$_2$ of the ethyl ester); MS: m/z.

[N-(pentafluorobenzoyl)-4-piperidylidenyl]-acetic acid, 18

The ester 16 (1.2 g, 3.44 mmol) was dissolved in methanol (15 ml) and aqueous sodium hydroxide (26 mL, 0.2 N) was added. The reaction mixture was heated under reflux for 2.5 h, and then poured over ethyl acetate, the aqueous layer was acidified with 10% HCl, and the product was extracted with CHCl$_3$. The dried CHCl$_3$ (over anhydrous Na$_2$SO$_4$) evaporated to yield a white solid (1.07 g, 96%) that was a one spot product on TLC (9:1 ethyl acetate:methanol); IR (film): 3500–2850, 1705, 1655 and 1625 cm$^{-1}$, $^1$H NMR (CDCl$_3$): δ 2.42 and 3.06 (two t, 4H, 2 CH$_2$ adjacent to the carboxylic acid), 3.40 and 3.83 (two t, 4H, 2 CH$_2$ adjacent to the N), 5.73 (br, s, 1H, vinylic proton), and 9.83 (s, 1H, carboxyl proton); MS: m/z 335 (M$^+$), 294, 195 and 167.

[N-(pentafluorobenzoyl)-4-piperidylidenyl]-acetic acid glycol, 4

The olefinic acid, 18 (1.07 g, 3.19 mmol) was dissolved in dry THF (26 mL) and osmium tetroxide (973 mg, 3.8 mmol) and pyridine (4 mL) were added. The reaction mixture was stirred at room temperature for 2 h under N$_2$. A solution of 10% sodium bisulfite (30 mL) was added, and the reaction mixture was stirred vigorously for 1 h, and then acidified (pH 3) with 10% HCl. The combined ethyl acetate extractions (15 mL×5) were washed with 10% sodium bisulfite, H$_2$O and dried over anhydrous Na$_2$SO$_4$. Evaporation afforded compound 9 (783 mg, 66%), which had the same mp, mixed mp and the spectral data of the dihydroxy acid prepared previously here.

N-(4'-methoxy-pentafluorobenzoyl)-4-piperidone ethylene, ketal, 28

N-(pentafluorobenzoyl)-4-piperidoneethylene ketal (500 mg, 1.48 mmol) was dissolved in methanol (5 ml) and sodium methoxide (119 mg, 2.2 mmol) were added. The reaction mixture was stirred at RT for 6 h, diluted with H$_2$O, and the aqueous layer was extracted 4 times with ethyl acetate. The organic layer was dried over anhydrous Na$_2$SO$_4$. Evaporation afforded colorless crystals which were recrystallized from ether/methanol (0.42 g, 82%); IR (film): 2960, 2880, 1655, 1030; $^1$H NMR (CDCl$_3$): δ 1.78 (overlap of two t, 4H, 2 CH$_2$ adjacent to the ketal), 3.48 and 3.96 (t, 4H, 2 CH$_2$ adjacent to the N), 4.05 (s, 4H, ethylene ketal), 4.18 (s, 3H, CH$_3$ of the ether).

N-(4'-methoxy-tetrafluorobenzoyl)-4-piperidone, 29 with R$_5$=CH$_3$

The ketal 28 (290 mg, 0.83 mmol) was dissolved in 5 ml dioxane and 38% HCl (0.5 ml) and 70% HClO$_4$ (0.5 ml) were added. The reaction mixture was stirred at room temperature for 3 hours. Ethyl acetate was added to the reaction mixture and the organic layer was washed with 10% NaHCO$_3$ and H$_2$O and dried over anhydrous Na$_2$SO$_4$. Evaporation of the solvent afforded a colorless oil which was three spots on TLC (3:7 ethyl acetate/hexane). Flash chromatography on silica gel (3:7 EtOAc/hexane) yielded 180 mg (71%) of the product.

Compound 7

Compound 7 is prepared from compound 5 the same as compound 6 is prepared from compound 4.

Compound 8

Coupound 6 is dissolved in 10% aqueous ethanol and hydrolyzed by 1.1 equivalents of sodium hydroxide at room temperature for 3 hr to give compound 8.

Compound 9

Compound 7 is reacted to form compound 9 the same as compound 6 is reacted to form compound 8.

Compound 10

Equimolar amounts of dry compound 8 and N-hydroxysuccinimide are dissolved in dry dioxane and reacted at 4° C. with 1.1 equivalents of N,N'-dicyclohexylcarbodiimide dissolved in dry dichloromethane. The reaction is stirred overnight at room temperature, and the resulting precipitate of dicyclohexyl urea is filtered out. The remaining solution is evaporated and the crude product is recrystallized.

Compound 11

Compound 11 is prepared from compound 9 the same as 10 is prepared pared from 8.

Compound 12

Thyroxine is reacted with a 10-fold molar excess of compound 10 in the presence of a 100-fold molar excess of 4-methylmorpholine at room temperature for 2 h in tetrahydrofuran. Evaporation gives a residue of compound 12.

Compound 13

Compound 13 is prepared from compound 11 the same as 12 is prepared from 10.

Compound 19

Compound 19 is prepared from compound 16 the same as 18 is prepared from 15.

Compounds 20-27

| Synthesis | Synthesis the same as: |
|---|---|
| 18 → 20 | 4 → 6 |
| 19 → 21 | 4 → 6 |
| 20 → 22 | 15 → 18 |
| 21 → 23 | 15 → 18 |
| 22 → 24 | 8 → 10 |
| 23 → 25 | 8 → 10 |
| 24 → 26 | 10 → 12 |
| 25 → 27 | 11 → 13 | p-aminocinnamic acid methyl ester,

A mixture of p-aminocinnamic acid (4.42 g) and sulfuric acid (10 drops) in 100 ml of methanol was refluxed for 15 hrs. The methanol was evaporated to dryness and chloroform (15 ml) was added. The solid which separated was filtered and washed with acetone, 2.84 g.

p-[(N-pentafluorobenzoyl, N-methyl)-aminol]-acetophenone, 30a p-Aminoacetophenone (1.35 g, 10 mmol) was dissolved in dry benzene (20 mL), and triethylamine (3 mL) was added, followed by addition of pentafluorobenzoyl chloride (2.31 g, 10 mmol). The reaction mixture was stirred at room temperature for 30 min under $N_2$. The mixture was diluted with EtOAc, and 10% HCL was added to acidify the aqueous layer. The organic layer was washed with 10% $NaHCO_3$, $H_2O$ and dried over anhydrous $Na_2SO_4$. Evaporation of the solvent gave a quantitative yield of an intermediate product, which was crystallized from acetone to afford yellowish crystals (one spot on TLC). Methylation was carried out on this intermediate product (2.17 g, 6.6 mmol), dissolved in acetone (60 mL), with methyl iodide (9.4 g, 66 mmol) and potassiun carbonate (4.55 g, 33 mmol). The reaction mixture was stirred under $N_2$ at room temperature for 14 h. Water was added and the product was extracted with ethyl acetate. The organic extract was washed with water and dried over anhydrous $Na_2SO_4$. Evaporation of the solvent gave a white product which was purified by flash chromatography (25:75 EtOAc/hexane) to yield white crystals of the ketoamide product.

Methyl -p-[(N-pentafluorobenzoyl, N-methyl)-amino]-3-methyl -cinnamate, 30b

Dry sodium hydride (90 mg, 3.75 mmol) was suspended in dry THF (10 mL) and methyl diethyl phosphorane acetate (787 mg, 3.75 mmol) were added. The resulting yellow solution was stirred under $N_2$ at room temperature for 15 min, until the evolution of $H_2$ stopped. The above ketoamide (1.071 g, 3.1 mmol) was dissolved in THF (5 ml) and added to the reaction mixture which was refluxed for 16 h. The solvent was evaporated and the resulting brownish oil had 3 products besides the starting material (TLC 3:7 EtOAc/hexane). Preparative HPLC gave 300 mg (30%) of unreacted starting material and 470 mg (38%) of the product.

Compounds 31

Compounds 31 are prepared by the same procedures used in example 1 and the procedures used to prepare compounds 1-30.

5-[N-Phthalimido]-2-pentanone ethylene ketal

5-Chloro-2-pentanone ethylene ketal (8.0 g, 48.6 mmol) was dissolved in dry DMF (30 mL), and potassium phthalimide (9.0 g, 48.6 mmol) was added to the reaction mixture with stirring. After 2 h at 90° C., the reaction mixture was poured into ice-$H_2O$. The resulting white solid was filtered, washed with cold $H_2O$ and dried under vacuum giving a product that was one spot on TLC (3:7 ethyl acetate/hexane) (12.6 g, 95%); IR (KBr): 3060, 2980, 2890, 1775 and 1720 cm$^{-1}$; $^1$H NMR (CDCl$_3$): δ1.29 (s, 3H, CH$_3$), 1.75 (m, 4H, 2 CH$_2$), 3.68 (br t, 2H, CH$_2$ adjacent to the nitrogen), 3.88 (s, 4H, 2 CH$_2$ of ethylene ketal), and 7.62 (m, 4H, aromatic protons).

5-Amino-2-Pentanone

The above ketal (6.0 g, 21.8 mmol) was dissolved in ethanol (20 mL), and anhydrous hydrazine (2.8 g, 87.2 mmol) was added. The reaction mixture was refluxed for 45 min, forming a white solid. The solvent and unreacted hydrazine were evaporated under vacuum, and this solid was dissolved in $H_2O$ (30 mL), followed by addition of conc. HCl to pH 3. Phthaylhydrazide was formed as a white suspension which was filtered off and washed with $H_2O$ (4×15 mL). The filtrate was extracted with CHCl$_3$, and the aqueous layer was basified with 40% NaOH to pH 11 with cooling, giving a turbid solution. The product was extracted with CHCl$_3$ (5×30 mL) followed by drying over anhydrous Na₂SO₄. Evaporation of the solvent under reduced pressure gave an unstable, yellowish oil that was pure enough by TLC (5:5 ethyl acetate/hexane) to start the acylation reaction.

N-[Pentafluorobenzoyl]-5-amino-2-pentanone, 32

The preceding amino-ketone (1.03 g, 10 mmol) was dissolved in dry benzene (20 mL). Triethylamine (1.5 mL) was added. Pentafluorobenzoyl chloride (2.31 g, 10 mmol) was added dropwise with stirring over 10 min. The reaction mixture was stirred at room temperature for 30 min, and then acidified with 10% HCl. Ethyl acetate was added, and the organic layer washed with 10% NaHCO₃, H₂O, and dried over anhydrous Na₂SO₄. Evaporation of the solvent afforded a yellow oil which was purified by flash column chromatography (3:7 ethyl acetate/hexane) to give white crystals (1.65 g, 55%), IR (film): 3310, 3050, 2940, 1720, 1660 and 1520; $^1$H NMR (CDCl₃): $\delta$1.88 (q, 2H, CH₂-4), 2.2 (s, 3H, CH₃), 2.62 (t, 2H, CH₂-3), 3.4 (q, 2H, CH₂-5), and 6.9 (br t, 1H, N-H); MS: m/z.

N,N-[Dipentafluorobenzoyl]-5-amino-2-pentanone, 33

The above ketoamide, 32 (745 mg, 2.5 mmol) was dissolved in dry benzene (10 mL) and triethylamine (1 mL) was added. Pentafluorobenzoyl chloride was added dropwise with stirring over 10 min. The reaction mixture was stirred at room temperature for 30 min. Ethyl acetate (20 mL) was added, and the organic solvent was washed with 10% HCl, 10% NaHCO₃ and dried over anhydrous Na₂SO₄. The product was separated by flash column chromatography to give white crystals; IR (film): 2930, 1710, 1650 and 1510 cm$^{-1}$; $^1$H NMR (CDCl₃): $\delta$1.87 (q, 2H, CH₂-4), 2.08 (s, 3H, CH₃), 2.50 (t, 2H, CH₂-3), and 3.8 (t, 2H, CH₂-5); MS: m/z 489 [M+].

p-Pentafluorobenzyloxyacetophenone, 34

Pentafluorobenzyl bromide (1.044 g, 4 mmol) was dissolved in CH₂Cl₂ (25 mL), and p-hydroxyacetophenone (544 mg, 4 mmol) was added. An aqueous solution (50 mL) was prepared by dissolving NaOH (400 mg, 10 mmol), and tetrabutylammonium hydrogen sulfate (1.7 g, 5 mmol). The organic phase was added to the aqueous phase, and vigorous stirring was done at room temperature for 14 h. The organic layer was separated, and the aqueous layer was extracted with CHCl₃ (15 mL×3). The combined organic extract was washed with H₂O and dried over anhydrous Na₂SO₄. TLC (3:7 ethyl acetate/hexane) showed the product as a single spot. Evaporation of the solvent gave white crystals in a quantitative yield.

Pentafluorobenzyloxy-acetone, 36

Pentafluorobenzylbromide (1 g, 0.6 ml, 4 mmol) and 0.3 g, (4 mmol) of hydroxyacetone were dissolved in 40 ml of CH₂Cl₂. Tetrabutylammolum hydrogensulfate (1.7 g, 5 mmol) were added, followed by 0.4 g of NaOH (10 mmol) in 40 ml of H₂O. The reaction mixture was stirred for 5 hrs. at RT and the organic layer was then separated from the aqueous layer. Evaporation of the organic layer yielded a slightly yellow oil that was purified by flash column chromatography on silica with 25% ethyl acetate/75% hexane to yield the product as a colorless oil that was a single spot by TLC and had appropriate infrared charcteristics.

p-(p-n-Propoxytetrafluorobenzyloxy)acetophenone (37) and the corresponding ortho compound p-Pentafluorobenzyloxyacetophenone (300 mg, 0.95 mmole) was dissolved in n-propanol (10 ml) and sodium hydroxide solution in H₂O (1 ml, 5N, 5 mmole) was added. The reaction mixture was refluxed for 14 h. TLC (20% EtOAC:hexane) showed 2 products besides some starting material. Flash column chromatography was done on the evaporated reaction mixture to give 2 products: The ortho substituted minor product, eluting first, and the para substituted major product, eluting last.

p-(p-isopropoxytetrafluorobenzyloxy)-acetophenone, 38 p-Pentafluorobenzyloxyacetophenone (400 mg, 1.27 mmole) was dissolved in isopropanol (10 ml), and sodium hydroxide solution in H₂O (1.3 ml, 5N, 6.5 mmole) was added. The reaction mixture refluxed for 14 h, and TLC (20% EtOAC:hexane) showed one product beside some unrelated starting material. Evaporation of the solvent gave an oil which was purified by flash column chromatography to give pure product.

Pentafluorophenoxyacetone, 39

Pentafluorophenol (1 g, 5.5 mmol), 1-bromo-2,2-dimethoxypropane (1 g, 5.5 mmol) and tetrabutylammoniun hydrogen sulfate (1.86 g, 5.5 mmol) phase transfer catalyst were dissolved in CH₂Cl₂ (30 ml). KOH (2.8 g, 50 mmol) dissolved in H₂O (30 ml) was added. The reaction mixture was stirred at room temperature for two days. The organic layer was washed with 10% HCl (during this procedure the acetal was hydrolyzed to the product ketone), 10% NaHCO₃ and H₂O. The product was separated from unreacted starting material by flash chromatography on silica gel (ethyl acetate/hexane 25/75), yielding 0.16 g. (12%) of a colorless liquid. $^1$H NMR (CDCl₃): $\delta$2.32 (s, 3H, methyl group) 4.78 (s, 2H, methylene group).

Methyl-3-(p-pentafluorobenzyloxyphenyl)-3-methyl-prop-2-enoate, 42

Compound 42 was synthesized from compound 34 by the same procedures used to synthesize compound 30b from 30a.

Methyl -3-(m-pentafluorobenxyloxyphenyl)-3-methyl-prop-2-enoate, 43

Compound 43 was synthesized by the same procedures used to prepare compound 42.

m-Pentafluorobenzyloxy-$\beta$-methyl-cinnamic acid, 48

Ester 43 (1.11 g, 2.98 mmol) was dissolved in t-butanol and KOH (6 ml, 5N) was added. The reaction mixture was refluxed with stirring for 3 hrs. TLC showed that al 1 the starting material disappeared. The organic layer was separated and evaporated to give a white solid which was dissolved in H₂O (25 ml) and acidified with conc. HCl to yield the product as a white solid. Crystallization from methanol afforded colorless crystals, m.p. 139°–141°.

m-Pentafluorobenzyloxy-$\beta$-methyl-cinnamoyl chloride, 49

Carboxylic acid 48 (490 mg, 1.37 mmol) was dissolved in dry benzene (15 ml) and SOCl₂ (3 mL, 41.1 mmol) was added. The reaction mixture was refluxed for 15 hrs. Evaporation of the solvent followed by trituration with benzene (10 ml×3) to remove the excess SOCl₂ and distillation afforded a brownish oil that had the spectral characteristics (IR, NMR) of the acid chloride.

1-Bromo-3-pentafluorophenoxy-acetone, 50

Compound 50 can be prepared by treating compound 39, pentafluorophenoxy-acetone, with bromine in acetic acid, followed by evaporation and purification by flash column chromatography.

1-Bromo-3-pentafluorophenoxy-acetone methoxime, 50a

Compound 50 can be converted to its corresponding methoxine derivative of the keto group by heating it at 60°–100° C. in pyridine containing methoxyamine hydrochloride, followed by evaporation and distillation.

1-Hydroxy-3-pentafluorophenoxy-acetone, 51

Compound 50 can be hydrolyzed in aqueous sodiun hydroxide to yield compound 51.

1-Hydroxy-3-pentafluorophenoxy-acetone methoxime, 51a

This ketone-derived methoxime can be prepared by hydrolyzing compound 50a in aqueous sodium hydroxide. It can also be prepared from compound 51 by the same procedure used to convert compound 50 to 50a.

1-(Chlorodimethylsiloxy)-3-pentafluorophenoxy-acetone methoxime, 52

This compound can be prepared by reacting compound 51a with excess dimethylchlorosilane in pyridine, followed by filtration, evaporation and distillation.

α-Bromo-p-pentafluorobenzyloxyacetophenone, 53

This compound can be prepared from compound 34 by the same procedure used to convert compound 39 to 50.

p-n-Propoxytetrafluorophenoxy-acetone, 54

This α-(fluoroalkoxyphenoxy)-alkanone can be prepared by converting compound 39 to the corresponding isopropylidene derivative, subjecting this latter derivative to the same reaction used to convert compound 34 to compound 37, followed by acid hydrolysis to convert the isopropylidene group back to a keto group.

1-Ethoxy-1(chlorodifluoromethyl)-2,2,2-trifluoromethyl succinate, 57

Chloropentafluoroacetone is reacted with anhydrous ethanol in anhydrous ethyl ether to give the corresponding ethyl hemiketal, and this is reacted with succinic anhydride in the presence of pyridine to give, after purification by flash column chromatography, the product.

p-Propoxy-tetrafluorobenzyl bromide, 58

This compound can be prepared by reacting pentafluorotoluene with propanol and sodium hydroxide in water, as described for the preparation of compound 37, followed by bromination with N-bromosuccinimide.

p-Isopropoxy-tetrafluorobenzyl bromide, 59

This compound can be prepared by reacting pentafluorotoluene with isopropanol and sodium hydroxide in water, as described for the preparation of compound 38, followed by bromination with N-bromosuccinimide.

Propyl-pentafluorophenoxymethyl-ketone, 60

2-Pentanone is converted to 1-bromo-2-pentanone with bromine in acetic acid and then converted to the corresponding 2,2-dimethoxy ketal with 95% methanol/3% sulfuric acid. This ketal is then converted to the product by the same procedure used to prepare compound 39 from 1-bromo-2,2-dimethoxypropane.

Isopropyl-pentafluorophenoxymethyl-ketone, 61

This compound is prepared from isopropylmethylketone by the same procedure used to prepare compound 60 from 2-pentanone.

Release Kinetics for the Diol

At time zero, 0.2 ml of a 2.5 mM solution of the diol (1-6) was was vortexed with an equal volume of 0.5 M aqueous sodium periodate. Aliquots (0.02 ml) were taken as a function of time and analyzed directly by reversed-phase HPLC using an isocratic mobile phase of 35-45% acetonitrile/65-55% water, depending on the compound. Both the decreasing response for the diol or olefin peak, and the increasing response for the ketone cleavage product, 14, were monitored and plotted to define the reaction kinetics, unless noted otherwise. The diols 7-13 can be released by the same procedures. The alkylidene-protected diol can be released by the same procedures after prior hydrolytic removal of the alkylidene group with aqueous acid or base.

Release of the Epoxide

The epoxide group can be released to the ketone as described (J. P. Nagarkatti and K. R. Ashley, *Tetrahedron Letters* 46, 1973, pp. 4599–4600) with peroxyacetic acid in water.

Other Release Groups Yielding a Ketone Signal Compound

An alkylidene release group can be cleaved with peroxyacetic acid, and an amino-alcohol, hydroxy-keto, and amino-keto release groups can be cleaved with periodate, to yield a ketone signal compound.

Olefin Release

At time zero, 0.9 pg of the olefin 42 in 2 μof acetonitrile was added to an aqueous solution (50 μl) of sodium periodate/potassium permangnate (2.4 μmol periodate, 50 nmol permangnate), pH 8.0. One pmol of 4-[pentafluorobenzyloxy]-acetophenone was also added as an internal standard. The reaction mixture was kept at 40° C. for 1 hr. The solution was extracted with isooctane (50 μl) and centrifuged. One μl of clear isooctane layer was injected on to the GC fitted with an HP ultraperformance fused silica capillary column (50 m, 0.31 mm I.D., 5 u film). The initial column temperature was 120° C. and held for 2 min. followed by programming to 250° C. at a rate of 50° C./min. The injector was programmed immediately after injection from 30° C. to 150° C. at a rate of 180°/min. The recovery of the released ketone was 90% which was calculated from an external standard curve. The yield of the reaction was 95% based on the recovery of the internal standard.

TABLE I

Rates of glycol cleavage to form the ketone, 14

TABLE I-continued

| Glycol | Reaction conditions for cleavage with NaIO$_4$[a] | Rate constant (sec$^{-1}$ × 10$^3$) at 23° C. (and 60° C.)[b] |
|---|---|---|
| 1 | 50% CH$_3$CN/50% H$_2$O | 3.3 (5.6) |
| 2 | 25%    /75% | 0.048 |
|   | 50%    /50% | 0.011 (0.076) |
|   | 75%    /25% | 0.0024 |
| 3 | 25%    /75% | 0.037 |
|   | 50%    /50% | 0.015 (0.053) |
|   | 75%    /25% | 0.0026 |
| 4 | 50%    /50% | 9.2 |
| 5 | 50%    /50% | 1.4 |
| 6 | 50%    /50% | 6.9 |
| 1 | 50% Dioxane/50% H$_2$O | 2.1 |
|   | 50% CH$_3$OH/50% H$_2$O | 8.9 |
|   | 5% CH$_3$CN/95% 0.11 M aq Na phos., pH 7 | 45 |
|   | 5% CH$_3$CN/95% aq. 0.23 M NaNO$_3$ | 50[c] |
|   | 5% CH$_3$CN/95% aq. 3.2 M urea | 67[d] |

Footnotes for Table I

[a]At time zero, 0.2 ml of a 0.5 M aqueous sodium periodate solution was added rapidly followed by vortexing to 0.2 ml of a 2.5 mM solution of the glycol in various solvents to give the final compositions shown. The final concentration for the glycol was 1.25 mM. One exception to this was the experiment for 2 and 3 in which the final reaction mixture contained 75% acetonitrile. In this case, 0.1 ml of aqueous periodate was added to 0.3 ml of the glycol, giving a final glycol concentration of 1.8 mM.

[b]Aliquots of 0.01 ml of the reaction mixture were removed as a function of time and injected directly onto reversed phase HPLC to both stop the reaction and simultaneously determine the amounts of starting glycol and product ketone. These two compounds had equivalent responses by HPLC with absorbance detection at 254 nm; no other peaks were seen; and the mass balance remained unchanged throughout the reaction. Consistent with pseudo first-order kinetics, plots of ln (glycol peak area/ketone + glycol peak area) vs time were linear, and the absolute values for the correlation coefficients of these lines were greater than 0.98 in all cases except for 1 in 50% CH$_3$OH and in 5% CH$_3$CN/95% 0.11 M Na phosphate buffer, and 6 in 50% CH$_3$CN, where absolute r values were 0.93 to 0.95.

[c]This reaction was nearly complete by the time of the first HPLC analysis, allowing only a single kinetic point, done in triplicate, to be obtained, having a standard deviation of 0.007.

[d]Same as footnote c, with a standard deviation of 5.1.

What is claimed is:

1. A release tag compound for use in chemical analysis, said compound having the generalized formula:
   S—R$_e$—R$_x$ wherein:
S is a signal group comprising a moiety selected from the group consisting of alkyl radicals of 1–12 carbon atoms, alicyclic radicals of 3–7 carbon atoms, and phenyl radicals, said moiety containing at least one halogen, said signal group having the property that upon cleavage of said release tag compound at the R$_e$ group, signal group S is released in the form of a ketone which is sufficiently volatile for determination in the gas phase;

R$_e$ is a release group capable of undergoing cleavage to release signal group S, and comprises a linkage selected from the group consisting of

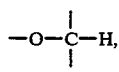
i)

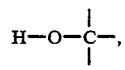
ii)

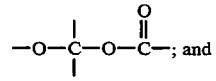
iii)
; and

R$_x$ is a reactivity group comprising a reactive functional group capable of bonding said release tag compound to a labelable substance;

and further,
in the release tag compound having the release group of formula i, the R$_x$ group is bonded to the oxygen atom of the formula and at least one signal group S is bonded to the carbon atom of the formula;

in the release tag compound having the release group of formula ii, the R$_x$ and S groups are both bonded to the carbon atom of the formula, and R$_e$ further comprises a keto, olefinic, alkynyl, or ester functionality located in a beta position relative to the OH group of the formula; and in the release tag compound having the release group of formula iii, the carbonyl group of the formula bears a moiety comprising the R$_x$ reactivity group, at least one signal group S is bonded to the non-carbonyl carbon atom of the formula, and an alkyl or aryl group is bonded to the non-carbonyl oxygen atom of the formula.

2. A release tag compound of claim 1 wherein release group R$_e$ has formula iii and reactivity group R$_x$ contains nitrogen, oxygen, bromine, or iodine.

3. A release tag compound of claim 1 wherein release group R$_e$ has formula iii, and the carbonyl group of the formula bears a moiety having the formula W(CH$_2$)$_n$R$_x$ wherein W is an oxygen atom or a CH$_2$ group, n is 1–3, and R$_x$ comprises a reactivity qroup.

4. A release tag compound of claim 3 wherein R$_x$ is —(CH$_2$)$_2$CO$_2$H.

5. The compound

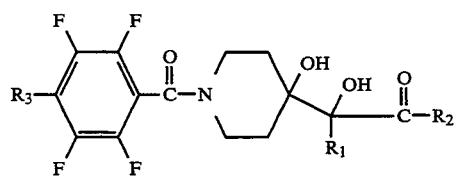

wherein
R$_1$ is H or CH$_3$,
R$_2$ is a reactivity group, and
R$_3$ is F or C$_1$–C$_6$ alkoxy.

6. The compound

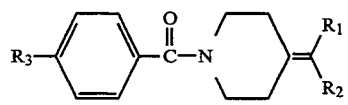

wherein
R$_1$ is H or CH$_3$,
R$_2$ is a reactivity group, and
R$_3$ is F or C$_1$–C$_6$ alkoxy.

7. The compound

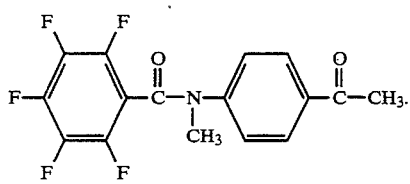

8. The compound

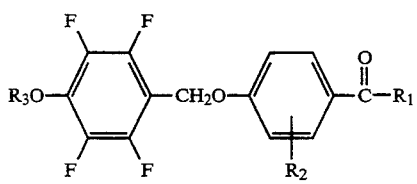

wherein R₁, R₂, and R₃ are $C_1$-$C_6$ alkyl.

9. The compound

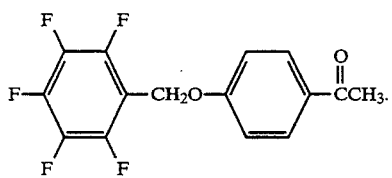

10. The compound

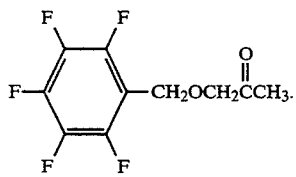

11. The compound

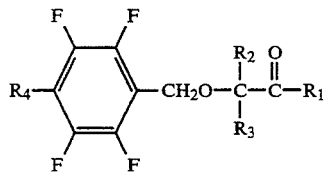

wherein
R₁ is $C_1$-$C_6$ alkyl or phenyl,
R₂ is H or $C_1$-$C_3$ alkyl,
R₃ is H or $C_1$-$C_3$ alkyl, and
R₄ is F or $C_1$-$C_6$ alkoxy.

12. The compound

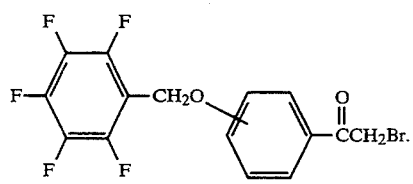

13. The compound

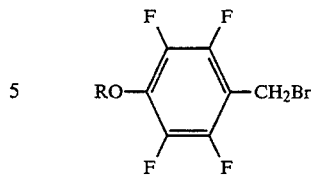

wherein R is propyl or isopropyl.

14. An assay comprising the steps of
1) contacting an analyte-containing sample with:
a) a release tag compound comprising:
a signal group, S, a release group Re, and a reactivity group Rx, group S being covalently linked to group Re, and group Re being further covalently linked to group Rx to define structure S-Re-Rx for said compound;
Rx further comprising a functional group capable of forming a covalent bond with another molecule;
Re further comprising a functionality selected from the group consisting of β-hydroxy ketones, β-hydroxy olefins, β-hydroxy alkynes, β-hydroxyesters, hemiketal esters, hemiketal carbonates, epoxides, alkylidenimes, β-aminoalcohols, β-(alkylamino)-alcohols, aikylidene-protected diols, α-hydroxy-ketos, and α-amino-ketos;
S further comprising a halogenated electron-absorbing organic group;
groups S and Re being mutually selected such that upon cleavage of said release tag at release group Re, signal group S is released in a volatile form suitable for electron capture determination in the gas phase;
or with
b) a molecular conjugate comprising a covalently linked combination of said release tag compound and a labelable substance;
2) incubating said contacted analyte-containing sample; and
3) determining the amount of released said signal group.

15. A release tag compound for use in chemical analysis, said compound having the generalized formula

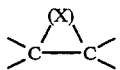

wherein:
S is a signal group comprising a moiety selected from the group consisting of alkyl radicals of 1–12 carbon atoms, alicyclic radicals of 3–7 carbon atoms, and phenyl radicals; said moiety containing fluorine; said signal group having the property that upon cleavage of said release tag compound at the $R_e$ group, signal group S is released in the form of a ketone which is sufficiently volatile for determination in the gas phase;
$R_e$ is a release group capable of undergoing cleavage to release signal group S, and comprises a linkage having the generalized formula

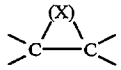

wherein X is selected from the group consisting of:
a) two OH radicals, to form a vicinal diol;
b) a covalent bond, to form an olefin;
c) an oxygen atom, to form an epoxide;
d) an NH group, to form an alkylidenimine;
e) one OH and one $N(R)_2$ radical wherein each R is H or an alkyl group, forming an α-hydroxy amine;
f) one OH and one ketone carbonyl, forming an α-hydroxy ketone;
g) one ketone carbonyl and one $N(R)_2$ radical wherein each R is H or an alkyl group, forming an α-keto amine; and
h) an alkylidene-protected diol; and $R_x$ is a reactivity group comprising a reactive functional group capable of bonding said release tag compound to a labelable substance.

16. A release tag compound for use in chemical analysis, said compound having the formula $$R_3\diagdown C\overset{(X)}{\underset{\phantom{C}}{\text{—}}}C\diagup R_1$$
$$R_4\diagup \phantom{C} \diagdown Y\text{—}Z$$

wherein $R_1$ is H, or an alkyl, aromatic, or alkyl-aromatic group;

$R_3$ is a signal group selected from the group consisting of $$C_6F_mG_n(CH_2)_pO-\underset{R_{17}}{\overset{R_{16}}{\underset{|}{\overset{|}{C}}}}-\quad \text{and} \quad C_6F_mG_n(CH_2)_pO-\bigcirc-$$

wherein m is 3–5, G is H, alkyl, haloalkyl, halogen, or alkoxy group, n is 1–2, p is 0–1, and $R_{16}$ and $R_{17}$ are each H or an alkyl group;

$R_4$ is an alkyl group;

the $$\diagup C\overset{(X)}{\underset{\phantom{C}}{\text{—}}}C\diagdown$$

portion of said release tag compound is a release group wherein X is selected from the group consisting of:
a) two OH groups, to form a vicinal diol;
b) a chemical bond, to form an olefin;
c) an oxygen atom, to form an epoxide;
d) an NH group, to form an alkylidenimine group;
e) one OH and one $N(R)_2$ radical wherein each R is H or an alkyl group, forming an a-hydroxy amine;
f) one OH and one ketone carbonyl, forming an α-hydroxy ketone;
g) one ketone carbonyl and one $N(R)_2$ radical wherein R is H or an alkyl group, forming an α-keto amine; and
h) an alkylidene-protected diol;

said release group being capable of undergoing cleavage to release the signal group as part of a ketone having the formula $R_3COR_4$;

Y is a linking moiety selected from the group consisting of: a chemical bond, a carbonyl group, an alkyl group, and an aromatic group; and Z is a reactivity group comprising a reactive functional group capable of covalently bonding said release tag compound to a labelable substance.

17. A release tag compound for use in chemical analysis, said compound having the formula $$R_3\diagdown C\overset{(X)}{\underset{\phantom{C}}{\text{—}}}C\diagup R_1$$
$$R_4\diagup \phantom{C} \diagdown Y\text{—}Z$$

wherein $R_1$ is H, or an alkyl, aromatic, or alkyl-aromatic group;

$R_3$ and $R_4$ each comprises at least one moiety selected from the group consisting of alkyl radicals of 1–12 carbon atoms, alicyclic radicals of 3–7 carbon atoms, and phenyl radicals; at least one said moiety containing at least one halogen or nitro substituent and being designated a signal group; $R_3$ also including a halophenoxy or alkoxyphenoxy radical in the position alpha to the carbon atom joining $R_3$ and $R_4$; and $R_4$ also comprising an alkyl radical;

the $$\diagup C\overset{(X)}{\underset{\phantom{C}}{\text{—}}}C\diagdown$$

portion of said release tag compound is a release group wherein X is selected from the group consisting of:
a) two OH groups, to form a vicinal diol;
b) a chemical bond, to form an olefin;
c) an oxygen atom, to form an epoxide;
d) an NH group, to form an alkylidenimine group;
e) one OH and one $N(R)_2$ radical wherein each R is H or an alkyl group, forming an α-hydroxy amine;
f) one OH and one ketone carbonyl, forming an α-hydroxy ketone;
g) one ketone carbonyl and one $N(R)_2$ radical wherein R is H or an alkyl group, forming an α-keto amine; and
h) an alkylidene-protected diol;

said release group being capable of undergoing cleavage to release the signal group as part of a ketone having the formula $R_3COR_4$;

Y is a linking moiety selected from the group consisting of: a chemical bond, a carbonyl group, an alkyl group, and an aromatic group; and Z is a reactivity group comprising a reactive functional group capable of covalently bonding said release tag compound to a labelable substance.

18. The compound

[structure: pentafluorinated (with $R_3$ substituent) benzoyl-N-piperidinone]

wherein $R_3$ is F or $C_1$–$C_6$ alkoxy.

19. The compound m-pentafluorobenzyloxy-β-methyl-cinnamic acid.

20. The compound m-pentafluorobenzyloxy-β-methyl-cinnamoyl chloride.

* * * * *

UNITED STATES PATENT AND TRADEMARK OFFICE
CERTIFICATE OF CORRECTION

PATENT NO. : 5,360,819
DATED : Nov. 1, 1994
INVENTOR(S) : Roger W. Giese

It is certified that error appears in the above-indentified patent and that said Letters Patent is hereby corrected as shown below:

Column 3, line 51, "Vol. 3 E. Gross" should read --Vol. 3, E. Gross--.

Column 5, line 65, "zoyimethionyl" should read --zoylmethionyl--.

Column 8, line 5, "absorbinq" should read --absorbing---.

Column 11, line 33, "under mile" should read --under mild--.

Column 17, line 59, "macromoiecules" should read ---macromolecules--.

Column 19, line 11, "glyco" should read --glycol--.

Column 19, line 26, "coenzynes" should read --coenzymes--.

Column 21, line 9, "compound A" should read --compound $\underset{\sim}{A}$--.

Column 23, line 26, "a allow oil" should read --a yellow oil--.

Column 23, line 36, ")-4-piperidylideny]" should read --)-4-piperidylidenyl].

Column 28, lines 27/28, "tetrabutylammoniun" should read --tetrabutylammonium--.

UNITED STATES PATENT AND TRADEMARK OFFICE
CERTIFICATE OF CORRECTION

PATENT NO. : 5,360,819
DATED : Nov. 1, 1994
INVENTOR(S) : Roger W. Giese

It is certified that error appears in the above-indentified patent and that said Letters Patent is hereby corrected as shown below:

Column 28, line 57, "al 1 the" should read --all the--.

Column 30, line 47, "$\underset{\sim}{42}$ in 2 $\mu$ of" should read --$\underset{\sim}{42}$ in 2 $\mu$l of--.

Column 34, line 45-50 (formula under Claim 15),

"  "  should read --$S-R_c-R_x$--.

Signed and Sealed this

Seventeenth Day of October, 1995

Attest:

BRUCE LEHMAN

*Attesting Officer*          *Commissioner of Patents and Trademarks*